US011896661B2

(12) United States Patent
Wan et al.

(10) Patent No.: US 11,896,661 B2

(45) Date of Patent: Feb. 13, 2024

(54) INFLUENZA VIRUS VACCINE AND METHOD OF MAKING

(71) Applicant: Mississippi State University, Starkville, MS (US)

(72) Inventors: Xiu-Feng Wan, Starkville, MS (US); Feng Wang, Starkville, MS (US)

(73) Assignee: Mississippi State University, Starkville, MS (US)

(*) Notice: Subject to any disclaimer, the term of this patent is extended or adjusted under 35 U.S.C. 154(b) by 650 days.

(21) Appl. No.: 16/608,662

(22) PCT Filed: Apr. 27, 2018

(86) PCT No.: PCT/US2018/029945

§ 371 (c)(1),
(2) Date: Oct. 25, 2019

(87) PCT Pub. No.: WO2018/201044

PCT Pub. Date: Nov. 1, 2018

(65) Prior Publication Data

US 2020/0188507 A1 Jun. 18, 2020

Related U.S. Application Data

(60) Provisional application No. 62/490,654, filed on Apr. 27, 2017.

(51) Int. Cl.

| | |
|---|---|
| ***A61K 39/145*** | (2006.01) |
| ***C07K 14/005*** | (2006.01) |
| ***C12N 9/24*** | (2006.01) |
| ***C12Q 1/70*** | (2006.01) |

(52) U.S. Cl.

CPC .......... *A61K 39/145* (2013.01); *C07K 14/005* (2013.01); *C12N 9/2402* (2013.01); *C12Q 1/70* (2013.01); *C12N 2760/16122* (2013.01); *C12N 2760/16134* (2013.01)

(58) Field of Classification Search

None

See application file for complete search history.

(56) References Cited

U.S. PATENT DOCUMENTS

| | | | |
|---|---|---|---|
| 10,172,934 | B2 | 1/2019 | Kawaoka et al. |
| 2008/0125347 | A1 | 5/2008 | Grabstein et al. |
| 2014/0221628 | A1 | 8/2014 | Wu et al. |

FOREIGN PATENT DOCUMENTS

| | | | |
|---|---|---|---|
| WO | WO2014151488 | A1 | 9/2014 |
| WO | WO2016196846 | A2 | 12/2016 |

OTHER PUBLICATIONS

Wen et al. "(96) A Y161F hemagglutinin substitution improves yields of a 2009 H1N1 influenza A vaccine virus in cells by increasing their binding affinities to alpha 2,3-linked and 2,6-linked sialic acid receptors" Glycobiology 26:1412-1413. (Year: 2016).*

Ye et al. "Error-prone pcr-based mutagenesis strategy for rapidly generating high-yield influenza vaccine candidates" Virology 283: 234-243. (Year: 2015).*

Wang et al. "Residue Y161 of Influenza Virus Hemagglutinin Is Involved in Viral Recognition of Sialylated Complexed from Different Hosts" J. Virology 86:4455-4462. (Year: 2012).*

Wang, et al. "Residue Y161 of Influenza Virus Hemagglutinin Is Involved in Viral Recognition of Sialylated Complexes from Different Hosts, "Journal of Virology, Apr. 30, 2012 (Apr. 30, 2012), vol. 86, No. 8, pp. 4455-4462.

Ye, et al. "Error-Prone PCR-Based Mutagenesis Strategy for Rapidly Generating High-Yield Influenza Vaccine Candidate," Virology, Apr. 17, 2015 (Apr. 17, 2015), vol. 482, pp. 234-243.

PCT International Search Report, PCT/US2018/029945 dated Aug. 9, 2018.

Wang et al., "Residue Y161 of Influenza Virus Hemagglutinin Is Involved in Viral Recognition of Sialylated Complexes from Different Hosts", vol. 86, Issue 8, Apr. 15, 2012.

Pica et al., "Environmental Factors Affecting the Transmission of Respiratory Viruses", Current Opinion in Virology, vol. 2, Issue 1, Feb. 2012, pp. 90-95.

Imai et al., "Experimental Adaptation of an Influenza H5 HA Confers Respiratory Droplet Transmission to a Reassortant H5 HA/H1N1 Virus in Ferrets", Nature, vol. 486, Jun. 2012.

Schrauwen et al., "Host Adaptation and Transmission of Influenza A Viruses in Mammals", Emerging Microbes & Infections, vol. 3, Feb. 12, 2014, 10 pages.

Watanabe et al., "Characterization of H5N1 Influenza Virus Variants with Hemagglutinin Mutations Isolated from Patients", mBio, vol. 6, Issue 2, Apr. 2015, 15 pages.

Minor, Philip D., "Vaccines against Seasonal and Pandemic Influenza and the Implications of Changes in Substrates for Virus Production", Clinical Infectious Diseases, vol. 50, Issue 4, Feb. 15, 2010, pp. 560-565.

Wen F, Li L, Zhao N, Chiang M-J, Xie H, Cooley J, Webby R, Wang PG, Wan X-F. 2018. AY161F hemagglutinin substitution increases thermostability and improves yields of 2009 H1N.

GeneMorph II EZClone Domain Mutagenesis Kit Instruction Manual.

Taubenberger et al., "Influenza: The Once and Future Pandemic", Public Health Reports, vol. 125, Supplement 3, 2010, 12 pages.

Thompson et al., "Influenza-Associated Hospitalizations in the United States", JAMA, vol. 29, No. 11, Sep. 15, 2004, pp. 1333-1340.

(Continued)

*Primary Examiner* — Sudhakar Katakam

*Assistant Examiner* — Zachary J Miknis

(74) *Attorney, Agent, or Firm* — Butler Snow LLP

(57) ABSTRACT

A composition for increasing vaccine yields due to increased virus growth in mutation comprising a vaccine strain bearing the Y161F mutation in hemagglutinin (HA). Y161F in HA increases HA thermostability without changing its original antigenic properties and enhances its binding affinity in the vaccine production platforms used in influenza vaccine manufacturing. A method for optimizing preparation of influenza vaccine seed strains which can further lower the cost of vaccines and increase profits for the vaccine companies, and also maintain antigenic stability during vaccine deliveries.

4 Claims, 17 Drawing Sheets

Specification includes a Sequence Listing.

(56) References Cited

OTHER PUBLICATIONS

Muennig et al., "Cost-Effectiveness of Vaccination Versus Treatment of Influenza in Healthy Adolescents and Adults", Clinical Infectious Diseases, vol. 33, Issue 11, 2001, pp. 1879-1885.

Lambert et al., "Influenza Vaccines for the Future", The New England Journal of Medicine, vol. 363, No. 21, Nov. 18, 2010, pp. 2036-2044.

Fulvini et al., "Gene Constellation of Influenza A Virus Reassortants with High Growth Phenotype Prepared as Seed Candidates for Vaccine Production", PLoS One, vol. 6, Issue 6, e20823, Published: Jun. 2011, 11 pages.

Milián et al., "Current and Emerging Cell Culture Manufacturing Technologies for Influenza Vaccines", Hindawi Publishing Corporation, BioMed Research International, vol. 2015, Article ID 504831, 12 pages.

Gambaryan et al., "Effects of Host-Dependent Glycosylation of Hemagglutinin on Receptor-Binding Properties of H1 N1 Human Influenza A Virus Grown in MDCK Cells and in Embryonated Eggs", Virology, vol. 247, Issue 2, Aug. 1, 1998, pp. 170-177.

Katz et al., "Host cell-Mediated Variation in H3N2 Influenza Viruses", Virology, vol. 156, Issue 2, Feb. 1987, pp. 386-395.

Meyer et al., "Influence of Host Cell-Mediated Variation on the International Surveillance of Influenza A (H3N2) Viruses", Virology, vol. 196, Issue 1, Sep. 1993, pp. 130-137.

Schild et al., "Evidence for Host-Cell Selection of Influenza Virus Antigenic Variants", Nature, vol. 303, Jun. 23, 1983, pp. 706-709.

Davies et al., "Egg allergy, influenza vaccine, and immunoglobulin E antibody", Journal of Allergy and Clinical Immunology, vol. 57, Issue 4, Apr. 1976, pp. 373-383.

Perdue et al., "The future of cell culture-based influenza vaccine production", Expert Review of Vaccines, vol. 10, No. 8, 2011, pp. 1183-1194.

Chu et al., "Conversion of MDCK Cell line to Suspension Culture by Transfecting with Human siat7e gene and its application for influenza virus Production", Proceedings of the National Academy of Sciences of the United States of America, vol. 106, No. 35, Sep. 1, 2009, pp. 14802-14807.

Halperin et al., "Safety and immunogenicity of a trivalent, inactivated, mammalian cell culture-derived influenza vaccine in healthy adults, seniors, and children", Vaccine, vol. 20, Issues 7-8, Jan. 15, 2002, pp. 1240-1247.

Kistner et al., "Development of a Mammalian Cell (Vero) Derived Candidate Influenza Virus Vaccine", Vaccine, vol. 16, Issues 9-10, 1998, pp. 960-968.

Lau et al., "Abortive Infection of Vero Cells by an Influenza A Virus (FPV)", Virology, vol. 212, Issue 1, Sep. 10, 1995, pp. 225-231.

Nakamura et al. "Protein Synthesis in Vero Cells Abortively Infected with Influenza B Virus", Journal of General Virology header logo vol. 56, Issue 1, Published: Sep. 1, 1981, pp. 199-202.

Rambhia et al., "Mass vaccination for the 2009 H1N1 pandemic: approaches, challenges, and recommendations", Biosecurity and Bioterrorism: Biodefense Strategy, Practice, and Science, vol. 8, No. 4, 2010, pp. 321-330.

Cobbin et al., "The Source of the PB1 Gene in Influenza Vaccine Reassortants Selectively Alters the Hemagglutinin Content of the Resulting Seed Virus", ASM Journals, Journal of Virology, vol. 87, No. 10, Mar. 6, 2013, pp. 5577-5585.

Hoffmann et al., "Eight-Plasmid System for Rapid Generation of Influenza Virus Vaccines", Vaccine, vol. 20, Issues 25-26, Aug. 19, 2002, pp. 3165-3170.

Hu et al.," A Vero-Cell-Adapted Vaccine Donor Strain of Influenza A Virus Generated by Serial Passages", Vaccine, vol. 33, Issue 2, Jan. 3, 2015, pp. 374-381.

Liu et al., "Efficacy of a High-Yield Attenuated Vaccine Strain Wholly Derived from Avian Influenza Viruses by use of Reverse Genetics", Veterinary Microbiology, vol. 161, Issues 1-2, Dec. 28, 2012, pp. 43-48.

Suphaphiphat et al., "Mutations at Positions 186 and 194 in the HA gene of the 2009 H1N1 Pandemic influenza Virus Improve Replication in Cell Culture and Eggs", Virology Journal, vol. 7, Article No. 157, Jul. 14, 2010, 5 pages.

Hamamoto et al., "High Yield Production of Influenza Virus in Madin Darby canine kidney (MDCK) cells with stable knockdown of IRF7", PloS one, vol. 8, Issue 3, e59892, Mar. 26, 2013, 12 pages.

Brandau et al., "Thermal Stability of Vaccines", Journal of Pharmaceutical Sciences, vol. 92, Issue 2, Feb. 2003, pp. 218-231.

O'Donnell et al. "The Matrix Gene Segment Destabilizes the Acid and Thermal Stability of the Hemagglutinin of Pandemic live Attenuated Influenza Virus Vaccines", Journal of Virology, vol. 88, No. 21, Nov. 1, 2014, pp. 12374 -12384.

Rudneva et al., "Effects of Hemagglutinin Amino Acid Substitutions in H9 influenza A Virus Escape Mutants", Archives of Virology, vol. 161, Sep. 01, 2016, pp. 3515-3520.

Ilyushina et al., "Adaptation of Pandemic H1N1 Influenza Viruses in Mice", Journal of Virology, vol. 84, No. 17, Sep. 1, 2010, pp. 8607-8616.

Adamo et al., "Optimizing Viral Protein Yield of Influenza Virus Strain A/Vietnam/1203/2004 by Modification of the Neuraminidase Gene", Journal of Virology, vol. 83, No. 9, May 1, 2009, pp. 4023-4029.

Ye et al., "Error-Prone Pcr-Based Mutagenesis Strategy for Rapidly Generating High-Yield Influenza Vaccine Candidates", Virology, vol. 482, Aug. 2015, pp. 234-243.

WHO Global influenza surveillance Network, "Manual for the laboratory diagnosis and virological surveillance of influenza", vol. xii. Geneva : Organization, 2011, 153 pages.

Li et al., "Efficient Chemoenzymatic Synthesis of an N-glycan Isomer Library", Chemical science, vol. 6, 2015, pp. 5652-5661.

Wu et al., "Identification of the Binding Roles of Terminal and Internal Glycan Epitopes using Enzymatically Synthesized N-Glycans Containing Tandem Epitopes", Organic & Biomolecular Chemistry vol. 14, 2016, pp. 11106-11116.

Xiong et al., "Receptor Binding by an H7N9 Influenza Virus from Humans", Nature, vol. 499, Jul. 25, 2013, pp. 496-499.

Edgar, Robert C., "Muscle: Multiple Sequence Alignment with High Accuracy and High Throughput", Nucleic Acids Research, vol. 32, Issue 5, Mar. 19, 2004, pp. 1792-1797.

Hall, Thomas A., "BioEdit: a User-Friendly Biological Sequence Alignment Editor and Analysis Program for Windows 95/98/NT", Nucleic Acids Symposium Series, vol. 41, Issue 2, 1999, pp. 95-98.

Skehel et al., "Receptor Binding and Membrane Fusion in Virus Entry: the Influenza Hemagglutinin", Annual Review of Biochemistry, vol. 69, 2000, pp. 531-569.

Hartgroves et al., "Rapid Generation of a Well-Matched Vaccine Seed from a Modern Influenza A virus Primary Isolate without recourse to eggs", Vaccine, vol. 28, Issue 17, Apr. 9, 2010, pp. 2973-2979.

Chen et al., "Generation of live Attenuated Novel Influenza Virus A/California/7/09 (H1N1) Vaccines with High Yield in Embryonated Chicken Eggs", Jounal of Virology, vol. 84, No. 1, Jan. 2010, pp. 44-51.

Chen et al., "Development of a High-Yield live Attenuated H7N9 Influenza Virus Vaccine that Provides Protection Against Homologous and Heterologous H7 wild-type viruses in ferrets", Journal of Virology, vol. 88, Issue 12, 2014, pp. 7016-7023.

Lugovtsev et al., "Mutational pattern of influenza B viruses adapted to high growth replication in embryonated eggs.", Virus Research, vol. 109, Issue 2, May 2005, pp. 149-157.

Robertson et al., "The development of vaccine viruses against pandemic A(H1N1) influenza", Vaccine vol. 29, Issue 9, Feb. 17, 2011, pp. 1836-1843.

Yasugi et al., "Frequency of D222G and Q223R Hemagglutinin Mutants of Pandemic (H1N1) 2009 Influenza Virus in Japan between 2009 and 2010", PLoS One, vol. 7, Issue 2, Feb. 2012, e30946, 6 pages.

Govorkova et al., "African Green Monkey Kidney (Vero) Cells Provide an Alternative Host Cell System for Influenza A and B Viruses", Jounal of Virology, vol. 70, No. 8, Aug. 1996, pp. 5519-5524.

(56) References Cited

OTHER PUBLICATIONS

Ito et al., “Differences in Sialic Acid-Galactose linkages in the Chicken Egg Amnion and Allantois Influence Human Influenza Virus Receptor Specificity and Variant Selection”, Journal of virology, vol. 71, No. 4, Apr. 1997, pp. 3357-3362.
Seo et al., “Characterization of a Porcine Lung Epithelial Cell Line Suitable for Influenza Virus Studies”, Journal of Virology, vol. 75, No. 19, Oct. 2001, pp. 9517-9525.
Aich et al., “Glycomics-Based Analysis of Chicken Red Blood Cells Provides Insight into the Selectivity of the Viral Agglutination Assay”, The FEBS journal, vol. 278, Mar. 2011, pp. 1699-1712.
Chen et al. “The Receptor Binding Specificity of the live Attenuated Influenza H2 and H6 Vaccine Viruses Contributes to Vaccine Immunogenicity and Protection in Ferrets”, Journal of virology, vol. 86 Issue 5, Mar. 1, 2012, pp. 2780-2786.
Ito et al., “Receptor Specificity of Influenza A Viruses Correlates with the Agglutination of Erythrocytes from Different Animal Species”, Virology, vol. 227, Issue 2, Jan. 20, 1997, pp. 493-499.
Ovsyannikova et al. “Turkey Versus Guinea Pig Red Blood Cells: Hemagglutination Differences Alter Hemagglutination Inhibition Responses Against Influenza A/H1N1”, Viral Immunology, vol. 27, No. 4, May 14, 2014, pp. 174-178.

* cited by examiner

| | 3'SLN | 6'SLN |
|---|---|---|
| HA-WT | 5.99 | 2.06 |
| HA-161F | -6.99 | -11.89 |

```
          ....|....| ....|....| ....|....| ....|....| ....|....|
                 160        170        180        190        200
H1        NHDSNKGVTA ACPHAGA-KS FYKNLIWLVK -KG-NSYPKL SKSYINDKGK
H2        QHTTTGG-SQ ACAVSGN-PS FFRNHVWLTK -KG-NSYPKL KGSYNNTSGE
H3        TGATQNGTSS ACIRRSK-NS FFSRLNWLT- HLN-FKYPAL NVTMPNNEQF
H4        STVKQNGKSG ACKRANV-ND FFNRLNWLT- KSDGNAYPLQ NLTKINNGDY
H5        NHDASSGVSS ACPYNGR-SS FFRNVVWLIK -KN-NAYPTI KRTYNNTNVE
H6        GVDTSSGVTQ ACPYNSG-SS FYRNLLWIIS TKS-AAYPVI KGTYKNTGNQ
H7        SGIRTNGATS ACRRSG--SS FYRAEHKWLLS NSDNAAFPQM TKSYRNPRNK
H8        VTSS--GTSK ACNASTGGQS FYRSINWLTK KKP-DTYQFN NHDSNKGVTA
H9        VTYS--GTSK ACSDS----- FYRSHRWLTQ K-N-NAYPIQ DAQYTNNQEK
H10       SSINSAGTTK ACMRNGG-NS FYAELEWLVS KSKGQNFPQT TNTYRNTDSA
H11       AVNSGAGVTA ACKFG-SSNS FFRNHVWLIH Q-S-GTYPVI RRTFNNTKGR
H12       VTYT--GTSK ACNNTSNKGS FYRSHRWLTL K-S-GQFPVQ TDEYKNTRDS
H13       EVND--GVSS ACKDK-GASS FYRNLVWFVK R-G-NTYPVI RVGYNNTTGR
H14       NGVKVDGSSS ACLRGGR-NS FFTRLNWLT- KATNGNYGPI NVTKENTGSY
H15       SGIRTDGATS ACKRTA--SS FYRSEHKWLSS SMNNQVFPQL NQTYRNTRKE
H16       NVLD--GVTA SCLDR-GASS FYRNLVWLVK Q-N-GKYPII KGDYNNTTGR
H17       GVT-TNNVDQ TCPFEGK-PS FRYNLNWIQG ----NSGLPF NIEIKNPTSN
H18       DVT-TNNVDS ACPYDTNGAS FYRNLNWVQQ ----NKGKQL IFHYQNSENN
```

FIG. 4A

Supplementary Table 1. Glycan-Binding Affinity of rg-wt and rg-Y161F

| Glycan | rg-WT Mean RFU | ST | CV | rg-Y161F Mean RFU | ST | CV |
|---|---|---|---|---|---|---|
| N000 | 514 | 554.0210886 | 1.07786204 | 242 | 217.1276122 | 0.897221538 |
| N001 | 167 | 153.3636202 | 0.918345031 | 155 | 68.38835183 | 0.441215173 |
| N002 | 168 | 112.1605991 | 0.667622614 | 6063 | 1052.12927 | 0.173532784 |
| N003 | 4733 | 1040.572615 | 0.219854768 | 3254 | 697.6281005 | 0.214390934 |
| N004 | 119 | 87.78382539 | 0.737679205 | 121 | 49.77850942 | 0.41139264 |
| N005 | 169 | 171.6617799 | 1.015750177 | 24816 | 2895.1951 | 0.116666469 |
| N010 | 292 | 223.6563584 | 0.765946433 | 189 | 93.11372974 | 0.492665237 |
| N011 | 178 | 161.6099213 | 0.907920906 | 141 | 84.58368637 | 0.5998843 |
| N012 | 81 | 49.15282291 | 0.606824974 | 2503 | 111.1726885 | 0.044415776 |
| N013 | 3093 | 1951.742982 | 0.631019393 | 492 | 139.9242652 | 0.284398913 |
| N014 | 137 | 78.80038071 | 0.575185261 | 170 | 148.825625 | 0.875444853 |
| N015 | 72 | 36.21831949 | 0.503032215 | 12609 | 2617.258184 | 0.207570639 |
| N020 | 196 | 183.9561542 | 0.938551807 | 133 | 126.7886693 | 0.953298266 |
| N021 | 90 | 99.93681337 | 1.110409037 | 183 | 142.6918591 | 0.779736935 |
| N022 | 161 | 84.24646382 | 0.523269962 | 2488 | 353.1734701 | 0.141950752 |
| N023 | 5725 | 1004.459855 | 0.175451503 | 671 | 306.4047976 | 0.456639043 |
| N024 | 173 | 124.8926205 | 0.721922662 | 125 | 147.7368155 | 1.181894524 |
| N025 | 86 | 75.43120486 | 0.877107033 | 10255 | 1698.870056 | 0.165662609 |
| N030 | 193 | 101.8155194 | 0.527541552 | 113 | 51.72394674 | 0.457734042 |
| N031 | 228 | 193.0398923 | 0.846666194 | 140 | 142.5436775 | 1.018169125 |
| N032 | 155 | 72.9065612 | 0.470364911 | 3268 | 1320.528341 | 0.40407844 |
| N033 | 4219 | 1053.200962 | 0.249632842 | 411 | 270.542911 | 0.658255258 |
| N034 | 136 | 85.42130882 | 0.628097859 | 228 | 268.7547209 | 1.178748776 |
| N035 | 218 | 163.3859439 | 0.749476807 | 13403 | 2731.912785 | 0.203828455 |
| N040 | 233 | 189.9246342 | 0.815127185 | 384 | 592.6547055 | 1.543371629 |
| N041 | 145 | 132.8855397 | 0.916451998 | 54 | 65.64043469 | 1.215563605 |
| N042 | 146 | 156.0790398 | 1.069034519 | 2648 | 1043.086845 | 0.393914972 |
| N043 | 7669 | 972.9189929 | 0.126863867 | 6093 | 1122.519918 | 0.184231071 |
| N044 | 102 | 90.89279399 | 0.891105823 | 92 | 47.81108658 | 0.519685724 |
| N045 | 230 | 148.6001346 | 0.646087542 | 21475 | 4478.814028 | 0.208559443 |
| N050 | 165 | 128.3495228 | 0.777875896 | 176 | 185.0207196 | 1.051254088 |
| N051 | 140 | 121.8304833 | 0.870217738 | 217 | 127.7748019 | 0.588823972 |
| N052 | 177 | 153.4309834 | 0.866841714 | 4560 | 1013.408786 | 0.222238769 |
| N053 | 7601 | 1377.35776 | 0.181207441 | 7492 | 730.1105852 | 0.097452027 |
| N054 | 209 | 130.6598638 | 0.625166812 | 279 | 129.5830493 | 0.464455374 |
| N055 | 199 | 114.7135563 | 0.576450032 | 19927 | 1692.217411 | 0.084920832 |
| N111 | 203 | 111.6382551 | 0.549942143 | 136 | 35.85340523 | 0.26362798 |
| N112 | 298 | 215.4766035 | 0.723075851 | 5532 | 2011.023388 | 0.363525558 |

| A | B | C | D | E | F | G | H |
|---|---|---|---|---|---|---|---|
| N113 | 7821 | 2316.139324 | 0.296143629 | 462 | 291.329138 | 0.63058255 |
| N114 | 236 | 225.4386095 | 0.955248345 | 142 | 123.484412 | 0.869608535 |
| N115 | 211 | 246.8259846 | 1.169791396 | 13940 | 5095.90968 | 0.365560235 |
| N122 | 278 | 125.4762926 | 0.45135357 | 3098 | 997.6329318 | 0.322024833 |
| N123 | 180 | 103.4485379 | 0.5747141 | 151 | 184.6726834 | 1.222997903 |
| N124 | 125 | 43.09717702 | 0.344777416 | 113 | 40.75986588 | 0.360706778 |
| N125 | 330 | 519.7093098 | 1.574876696 | 10961 | 3091.107482 | 0.282009623 |
| N134 | 211 | 132.0112369 | 0.625645672 | 5578 | 1370.346927 | 0.24566994 |
| N144 | 3566 | 560.6510501 | 0.15722127 | 103 | 75.10104305 | 0.72913634 |
| N155 | 366 | 377.8749352 | 1.032445178 | 11044 | 2922.801789 | 0.264650651 |
| N211 | 163 | 133.6843297 | 0.820149262 | 146 | 93.45533693 | 0.640105047 |
| N212 | 241 | 142.8939 | 0.592920747 | 1535 | 583.1601552 | 0.379908896 |
| N213 | 1657 | 400.9965918 | 0.242001564 | 86 | 129.9806396 | 1.511402786 |
| N214 | 123 | 72.86631595 | 0.592409073 | 124 | 120.1010685 | 0.968557004 |
| N215 | 127 | 67.2718366 | 0.529699501 | 13799 | 2858.561765 | 0.207157168 |
| N222 | 220 | 284.1865584 | 1.291757084 | 9401 | 2904.195035 | 0.308924054 |
| N223 | 14795 | 1578.348884 | 0.106681236 | 5416 | 1634.223822 | 0.301739997 |
| N224 | 206 | 174.4660425 | 0.846922537 | 181 | 156.2544933 | 0.863284493 |
| N225 | 114 | 58.2285726 | 0.510776953 | 3959 | 1818.107551 | 0.459234037 |
| N234 | 465 | 272.6587611 | 0.586362927 | 5643 | 1547.522364 | 0.274237527 |
| N244 | 15494 | 1405.73977 | 0.090728009 | 271 | 116.5837324 | 0.430198275 |
| N255 | 150 | 123.9559061 | 0.826372708 | 4337 | 1640.067529 | 0.378157143 |
| N012G | 239 | 105.9144309 | 0.443156615 | 147 | 75.76916699 | 0.51543651 |
| N013G | 109 | 124.4422222 | 1.141671763 | 366 | 736.151728 | 2.011343519 |
| N015G | 146 | 84.62958506 | 0.579654692 | 87 | 89.17043606 | 1.024947541 |
| N022G | 126 | 91.46584062 | 0.72591937 | 218 | 149.5411872 | 0.685968749 |
| N023G | 141 | 74.0605608 | 0.525252204 | 186 | 210.8529503 | 1.133618013 |
| N025G | 174 | 94.83599879 | 0.545034476 | 148 | 124.159172 | 0.838913325 |
| NC | 181 | 234.1157121 | 1.293456973 | 132 | 99.37756286 | 0.752860325 |
| Marker | 11660 | 1243.800828 | 0.106672455 | 6348 | 763.6753237 | 0.120301721 |

FIG. 7
(Continued)

INFLUENZA VIRUS VACCINE AND METHOD OF MAKING

CROSS REFERENCE TO RELATED APPLICATIONS

This application claims priority to U.S. Provisional Application No. 62/490,654 filed on Apr. 27, 2017, the contents of which are incorporated herein by reference in its entirety.

GOVERNMENT SUPPORT STATEMENT

This invention was made with Government support under R01 AI116744 & P20 GM103646 awarded by the National Institutes of Health. The Government has certain rights in the invention.

SEQUENCE LISTING

The instant application contains a Sequence Listing which has been filed electronically in ASCII format and is hereby incorporated by reference in its entirety. Said ASCII copy, created on Apr. 19, 2023 is named 028186_184790_SLAmended.txt and is 104 kilobytes in size.

FIELD OF THE INVENTION

The present invention is generally directed toward an influence virus vaccine, and more particularly, it is directed towards an influenza virus vaccine comprising a Y161F mutant of influenza A and methods related to the same.

BACKGROUND OF THE INVENTION

Influenza A viruses (IAVs) cause seasonal outbreaks and occasional pandemic outbreaks among humans and pose challenges to public health. The viruses responsible for four pandemics have been characterized: one each in 1918 and 2009 caused by H1N1 IAVs, one in 1957 caused by an H2N2 IAV, and one in 1968 caused by an H3N2 IAV (Taubenberger et al., 2010). These pandemic outbreaks varied in impact, but each resulted in substantial mortality in a short time. Compared with pandemic outbreaks, seasonal influenza outbreaks are typically milder but still cause approximately 200,000 hospitalizations and 36.000 deaths each year in the United States alone (Thompson et al., 2004).

Vaccination has been the most efficient and economic strategy for preventing influenza virus infection and controlling the spread of disease (Muennig et al., 2001). Two types of virus-based influenza vaccines, inactivated and live-attenuated vaccines, are licensed in the United States, with egg-produced vaccine being the dominant source (Lambert et al., 2010; Fulvini et al., 2011). The egg-based platform for vaccine production has been used since the 1950s (Milian et al., 2015), but it has several disadvantages: first, passage of seed viruses in eggs can result in undesired egg-adapting mutations in the hemagglutinin (HA) that can lead to changes in viral antigenicity (Gambaryan et al., 1998; Katz et al., 1987; Meyer et al., 1993; Schild et al., 1983); second, due to reactogenicity concerns, egg grown vaccine is contraindicated for those with egg allergies (Davies et al., 1976); and third, rapidly scaling up egg production is not easily achievable. Cell-based vaccine production platforms do not have the same limitations (Perdue et al., 2011). All continuous cell lines, including Madin-Darby canine kidney (MDCK) cells and African green monkey kidney-derived Vero cells, must be certified before being approved by regulatory authorities for use in the production of influenza vaccines (Chu et al., 2009; Halperin et al., 2002; Kistner et al., 1998).

A high-yield vaccine seed strain is required for timely vaccine manufacture and is thus a critical component of a successful influenza vaccination program. Unfortunately, it is not uncommon that the vaccine strains recommended by the World Health Organization (WHO) have less than desirable yields in eggs, cells, or both (Lau et al., 2016; Nakamura et al., 1981). For example, the 2009 H1N1 pandemic seed strain was a low-yield strain, and it required almost 3 months for the WHO collaborative laboratories and vaccine companies to engineer the selected strain to meet the criteria required for vaccine production. Because of this delay, vaccine-derived immunity among the population arose after the peak of the second wave of the 2009 H1N1 pandemic (Rambhia et al., 2010). Therefore, quickly generating a high-yield vaccine seed virus is critical for rapid vaccine production and, thus, for effective influenza prevention and control. Adaptation of viruses to cells by multiple passaging or development of high-yield reassortant seeds using reverse genetics has been shown to be an effective way to increase yield of vaccine seed viruses (Cobbin et al., 2013; Hoffman et al., 2002; Hu et al., 2015; Liu et al., 2012) In addition, other studies have been performed to improve virus yields in cells by modifying the virus or the cell line. For example, Suphaphiphat et al. showed that mutations S186P and L194I in the receptor binding site (RBS) of the A/California/04/09 (CA/04) H1N1 HA increased growth of the virus by more than 10-fold in MDCK cells, and Hamamoto et al. reported that MDCK cells engineered with stable knockdown of interferon regulatory factor 7 increased IAV yields.

Thermostability is also important for vaccine quality, especially in low-income countries that lack the infrastructure to maintain a low and stable temperature during vaccine transportation (Brandua et al., 2003). The reduced thermostability of live attenuated vaccine for the 2009 H1N1 pandemic virus, may have been responsible for its restricted replication in vaccinated persons (O'Donnel et al., 2014). Mutations in HA protein can improve thermostability; for example, mutations S133N, T189A, N198D, and L226Q in the RBS of influenza HA were reported to be associated with a significant increase in thermostability of an H9 IAV (Rudneva et al., 2016).

Wild type influenza virus strains for vaccine usually do not grow well during vaccine production and the conventional methods for improving vaccine yields are time consuming. Further, little is known about genetic signature which can help improve vaccine yields but not change antigenic properties. Therefore a need exists for an optimized preparation of influenza vaccine seed strains, which can further lower the cost of vaccines and increase profits for the vaccine companies, and also maintain antigenic stability during vaccine deliveries.

SUMMARY OF THE INVENTION

High-yield vaccine seeds with thermostable antigens are required and necessary for influenza vaccine production. The present invention is directed to novel high-yield signatures for influenza viruses due to increased virus growth in mutation comprising a vaccine strain bearing the Y161F mutation in hemagglutinin (HA). Y161F in HA increases HA thermostability without changing its original antigenic properties and enhances its binding affinity in culls used in influenza vaccine manufacturing. Also disclosed herein is a method for optimizing preparation of influenza vaccine seed strains which can further lower the cost of vaccines and increase profits for the vaccine companies, and also maintain antigenic stability during vaccine deliveries.

BRIEF DESCRIPTION OF THE DRAWINGS

Further advantages of the invention will become apparent by reference to the detailed description of preferred embodiments when considered in conjunction with the drawings:

FIG. 1A depicts kidney cells and FIG. 1B depicts Vero cells. Each data point represents the mean virus yield (log 1 TCID50/ml) from three individually infected wells±the standard deviation. TCD50, 50% tissue culture infectious dose. FIG. 1C depicts a bar graph of the total protein of viruses propagated in Madin-Darby canine kidney cells, and FIG. 1D depicts a bar graph of 10-day-old embryonated chicken eggs.

FIG. 3A depicts the representative binding curve of H1N1 CA WT and Y161F toward alpha 2,6-linked sialic acid (SA2,6GA) receptor and FIG. 3B depicts the representative curve toward alpha 2,3-linked sialic acid (SA2,3GA) receptor. FIG. 3C depicts the binding response unit (nm) recorded at the 1,196 second time point (4 seconds before the start of dissociation) of sialic acid receptor concentrations titrated from 0.1 to 5 μg/ml (SA2,6GA) when loading with the biotin-labeled receptors. FIG. 3D depicts the binding response (nm) of 0.2 to 5 μg/ml (SA2,3GA). FIG. 3E-FIG. 3F depict three-dimensional structures of the hemagglutinin of wild-type (HA-WT) influenza A/California/04/09 (H1N1) virus and mutant viruse (HA-161F) in contact with avian-like receptor analog carbohydrate 3'-sialyl-N-acetyllactosamine (3'SLN) in FIG. 3E and human-like receptor avian 6'-sialyl-N-acetyllactosamine (6'SLN) FIG. 3F. FIG. 3G depicts the calculated PoseScore for viruses.

FIG. 4A-4F depict the effect of the Y161F mutation on replication of other IAVs and viral thermostability. Individually, FIG. 4A depicts the sequence alignment of hemagglutinin 1 (HA1) from 18 different influenza A virus HA subtypes (H1-H18, corresponding to SEQ ID Nos:35-52, respectively). Residues 161 (H3 numbering) are indicated by vertical rectangle. FIG. 4B depicts Y161 conserved in subtypes H1-H5, H8, H9, H11, H13, H14, and H16, F161 is conserved in subtypes H7, H10, H12, and H15. Each residue is numbered according to the H3 HA numbering. FIG. 4C depicts a lien graph, of the growth properties of canine subtype H3N8 influenza virus (cH3N8) and its hemagglutinin 1 (HA1) F161 mutant virus (cH3N8 Y161F). FIG. 4D depicts a line graph of the growth properties of influenza A/Puerto Rico/8/34 (H1N1) virus (PR8) and its HA1 F161 mutant virus (PR8 Y161F) in Madin-Darby canine kidney cells. Each data point represents the mean virus yield (log 10 TCID50/ml) from three individually infected wells±the standard deviation. FIG. 4E depicts a line graph showing the effect of 161F mutation (H1N1 161) on the thermostability of influenza A/California/04/09 (H1N1) virus. (H1N1 WT). FIG. 4F depicts a lien graph of the effect of 161F mutation (H3N8 161F) on the thermostability of influenza A/canine/Iowa/13628/2005 (H3N8) virus (H3N8). The viruses with equal HA titers were incubated at the indicated temperatures for 40 minutes and then titers were determined. TCID50, 50% tissue culture infectious dose.

FIG. 5A depicts a line graph of the percent change in body weight; each point represents the mean body weight of 5 mice per group. FIG. 5B depicts the percent surviving mice after challenge. *, p<0.0001 for PBS group versus WT group, as calculated by GraphPad Prism 5 software. FIG. 5C depicts a line graph of the histopathologic changes in hematoxylin and eosin-stained lung samples from groups of mice vaccinated with rg-CA/04 wild-type (WT). FIG. 5D depicts a line graph of the histopathologic changes in hematoxylin and eosin-stained lung samples from groups of mice vaccinated with rg-CA/04 161F (Mutant). FIG. 5E depicts a line graph of the histopathologic, changes in hematoxylin and eosin-stained lung samples from groups of mice vaccinated with virus vaccine; mock-vaccinated with phosphate buffered saline. FIG. 5**F depicts a line graph of the histopathologic changes in hematoxylin and eosin-stained lung samples from groups of mice serving as controls. Samples were collected 4 days after vaccinated and mock-vaccinated mice were challenged with 10 LD50 of mouse-adapted influenza A/California/04/09 (H1N1) virus. Magnification ×200.

FIG. 7 depicts glycan-binding affinity of rg-wt and rg-Y161F.

DETAILED DESCRIPTION

Figure 1A:
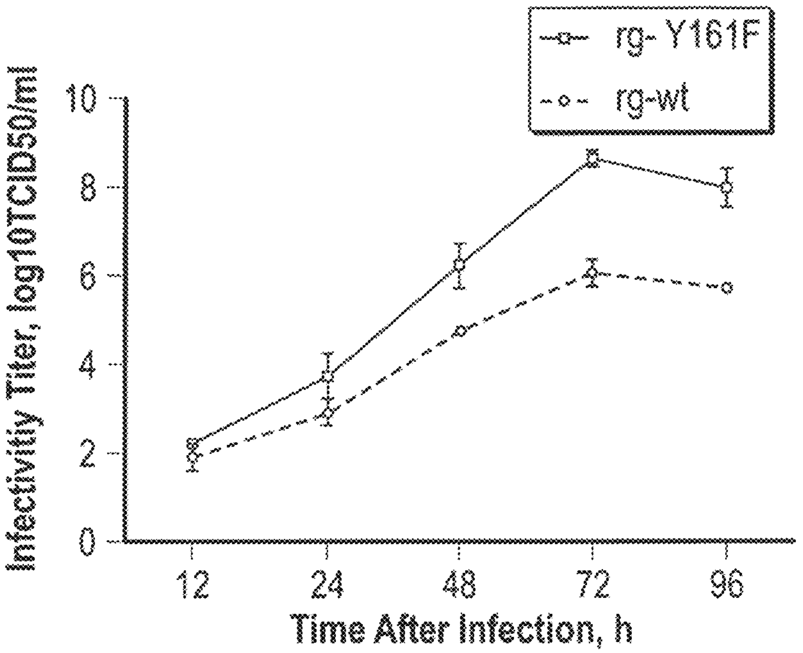
FIG. 1A-1D depict graphs of growth properties of wild-type (WT) and Y161F mutant viruses in Madin-Darby canine cells. Individually.

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Vaccination is the primary strategy for influenza prevention and control. However, vaccine seed viruses often do not grow efficiently during vaccine production. Disclosed herein is a vaccine strain bearing the Y161F mutation in HA that increases vaccine yields facilitating influenza vaccine manufacturing, which can further lower the cost of vaccines and increase profits for the vaccine companies, and also maintain antigenic stability during vaccine deliveries.

This invention discloses novel high-yield signatures for influenza viruses in vaccine production platforms such as continuous Madin-Darby canine kidney (MDCK) and Vero cells. Using influenza A(H1N1)pdm09 virus as the testing platform and an integrating error-prone PCR strategy, a Y161F mutation in the hemagglutinin (HA) was identified that not only enhanced the infectivity of the resultant virus by more than 300-fold, but also increased its thermostability without changing its original antigenic properties. Vaccine produced from the Y161F mutant fully protected mice against wild-type A(H1N1)pdm09 lethal challenge. Compared with A(H1N1)pdm09, the Y161F mutant had significantly higher avidity for avian-like and human-like receptor analogs. Of note, introduction of the Y161F mutation into the HA of seasonal H3N2 influenza A virus (IAV) and canine H3N8 IAV also increased yields and thermostability in MDCK cells and chicken embryotic eggs. Thus, residue F161 plays an important role in determining viral growth, and thermostability, which could be harnessed to optimize IAV vaccine seed viruses. Although a promising complement to current egg-based influenza vaccines, cell-based vaccines have one big challenge—high-yield vaccine seeds for production. A molecular signature-Y161F in hemagglutinin (HA) was identified that resulted in increased virus growth in mutation not only increased HA thermostability, but also enhanced its binding affinity Madin-Darby canine kidney and Vero cells, two commonly used cell lines in influenza vaccine manufacturing. This Y161F to α2,6 and α2,3-linked Neu5Ac Thus, a composition for increasing vaccine yields comprising a vaccine strain bearing the Y161F mutation in HA and NA is disclosed herein.

Materials and Methods

Cells and Viruses.

Human embryonic kidney (293T) cells, MDCK cells, and Vero cells were purchased from American Type Culture Collection (Manassas, Va.). Cells were maintained at 37° C. with 5% CO2 in Dulbecco's Modified Eagle Medium (GIBCO/BRL, Grand Island, N.Y.) supplemented with 5% fetal bovine serum (Atlanta Biologicals, Lawrenceville, Ga.). penicillin-streptomycin, and amphotericin B (GIBCO/BRL, Grand Island, N.Y.). The HA gene of CA/04 was cloned into the vector pHW2000 and used as template for construction of the mutant library; mouse-adapted CA/04 (28) was used for challenge experiments in mice. Influenza A/Texas/S0/2012(H3N2) (TX/50) and A/canine/Iowa/13628/2005 (H3N8) virus (k9-H3N8) were used to validate the identified molecular markers.

The viruses generated by reverse genetics were propagated in MDCK cells and cultured at 37° C. with 5% $CO_2$ in Opti-MEM medium (GIBCO/BRL, Grand Island, N.Y.) supplemented with 1 μg/ml of TPCK (N-tosyl-L-phenylalanine chloromethyl ketone)-Trypsin (Sigma-Aldrich, St. Louis, Mo.), penicillin-streptomycin, and amphotericin B (GIBCO/BRL, Grand Island, N.Y.). Virus titers were determined by TCID50 in MDCK cells.

The viral total protein yield in eggs was tested as described by Adamo et al (29). Briefly, 10-day-old chicken embryotic eggs were infected with an influenza virus and then incubated at 37° C. for 72 h. The allantoic fluid of the infected eggs was collected for virus purification and quantification of protein concentrations as described below.

Extractions of RNA and Plasmids.

RNA was extracted by using an RNeasy Mini Kit (QIAGEN, Valencia, Calif.); the plasmids used for transfection were prepared by using the GeneJET Plasmid Miniprep kit (Thermo Scientific, Waltham, Mass.).

Mutant Generation Using epPCR-Based Reverse Genetics Strategy.

The mutant library with random mutations in HA RBSs was generated by epPCR as previously described (Ye et al., 2015). In brief, the randomly mutated short sequences (about 200 nucleotides) were used as primers in the site-directed mutagenesis with HA-pHW2000, leading to plasmids with random mutations in the HA RBSs. This strategy can avoid the need for a labor-intensive gene cloning process, and the HA-pHW2000 with mutations can be used directly in generating vaccine candidates (Ye et al., 2015). One day before transfection, 293T cells and MDCK cells were co-cultured in 24-well plates, using a 20:1 ratio of 293T cells to MDCK cells. The cell cultures were transfected with 125 ng of each of eight plasmids: a mutant HA gene, NA gene of CA/04, and 6 internal genes (PB2, PB1, PA, NP, M, and NS) of influenza A/PR/8/1934(H1N1) virus. Transfection was done using TransIT-LT Madison, Wis.) according to the manufacturer's instructions. In brief, TransIT-LT transfection reagent was mixed with DNA at 2.5 pill incubated at room temperature for 20 min, and then added to the cells. After 24 h, Opti-MEM medium (GIBCO/BRL) supplemented with 1 μg/ml of TPCK-trypsin (Sigma-Aldrich, St. Louis, Mo.) was added to the cells. After 72 h of incubation, supernatants were collected and titrated in MDCK cells.

For phenotype comparison, wild-type reassortant virus (rg-wt) was generated containing the wild-type HA and NA genes from CA/04 and six internal genes from A/Puerto Rico/8/34 (H1N1).

Site-Directed Mutagenesis.

The QuikChange 11 Site-Directed Mutagenesis Kit (Agilent Technologies, Santa Clara, Calif.) was used to create specific mutations in the HA gene. Forward primer 5'-CCACTTAAACTTCAAATTCCCAGCATT-GAACGTG-3' (SEQ ID NO:1) and reverse primer 5'-CACGTTCAATGCTGGGAATTTGAAGTT-TAAGTGG-3' (SEQ ID NO:2) was used to generate mutation Y161F in HA of TX/50, and forward primer 5'-CAAAATCTGGAAGCTCTTTCCCCACATT-GAATGTGAC-3' (SEQ ID NO:3) and reverse primer 5'-GT-CACATTCAATGTGGGGAAAGAGCTTCCAGATTTTG-3' (SEQ ID NO:4) was used to generate mutation Y161F in HA of k9-H3N8. To ensure the absence of unwanted mutations, Eurofinas (Louisville, Ky.) used Sanger sequencing to completely sequence all constructs.

Growth Kinetics.

To determine the growth kinetics of viruses, MDCK cells with were inoculated a testing virus at an MOI of 0.001 and then incubated the cells in 5% $CO_2$ at 37° C. for 1 h. The inocula were then removed and cells washed twice with phosphate-buffered saline (PBS). Opti-MEM I (GIBCO, Grand Island, N.Y.) containing TPCK-trypsin (1 μg/ml) was added to the cells, which were then incubated in 5% $CO_2$ at 37° C. At specified time points after inoculation, 200 μl of supernatant was collected from the incubated cells, aliquoted, and stored at −70° C. until use. Virus titers in supernatant collected at the different time points were determined by $TCID_{50}$ in MDCK cells.

Viral Protein Purification and Protein Concentration Quantification.

Viruses were purified from the cell supernatant or allantoic fluid by low-speed clarification (2,482×g, 20 min, 4° C.) to remove debris and then ultracentrifuged through a gradient of 30%-60% sucrose in a 70Ti Rotor (Beckman Coulter, Fullerton, Calif.) (100,000×g, 3 h, 4° C.). The virus band was collected and purified through a cushion of 30% sucrose in a 70Ti Rotor (100,000×g, 3 h, 4° C.). The virus pellet was resuspended in 200 μl of PBS, and the total amount of purified virion protein was determined by using the Pierce BCA Protein Assay Kit (Thermo Scientific, Rockford, Ill.).

HA and HI Assays.

HA and HI assays were performed by using 0.5% turkey erythrocytes as described by the WHO Global Influenza Surveillance Network Manual for the Laboratory Diagnosis and Virological Surveillance of Influenza (31). Guinea pig, chicken, horse, turkey, and dog (beagle) erythrocytes were obtained from Lampire Biological Products (Everett, Pa.). The erythrocytes were washed three times with 1×PBS (pH 7.2) and diluted to 0.5% for chicken, beagle, and turkey erythrocytes, 0.75% for guinea pig erythrocytes, and 1% for horse erythrocytes.

Glycan Microarray and Data Analyses.

The 66 N-glycans (Li et al., 2015) were printed on Ar-hydroxysuccinimide-derivatized slides as previously described (Wu et al., 2016). All glycans were printed in replicates of 6 in a subarray, and 8 subarrays were printed on each slide. All glycans were prepared at a concentration of 100 μM in phosphate buffer (100 mM sodium phosphate buffer, pH 8.5). The slides were fitted with an 8-chamber adapter (Grace Bio-Labs, Bend, Oreg.) to separate the subarray into individual wells for assay. Before assay, slides were rehydrated for 5 min in TSMW buffer (20 mM Tris-HCl, 150 mM NaCl, 0.2 mM $CaCl_2$), 0.2 mM $MgCl_2$, and 0.05% Tween-20) and blocked for 30 min in TSMWB buffer (TSMW buffer with 1% BSA). Viruses were purified by sucrose density gradient ultracentrifugation and titrated to about 1.0-$10^5$ HAU/ml. To 150 μl of virus, I added 15 μl of 1.0 M sodium bicarbonate (pH 9.0) and then incubated the mixture with 25 μg of Molecular Probes Alexa 488 Succinimidyl Esters (NHS esters) (Thermo Fisher Scientific, Inc., Waltham, Mass.) for 1 h at 25°C. After overnight dialysis against a 7 KDa Slide-A-Lyzer MINI Dialysis Devices (Thermo Fisher Scientific, Inc., Waltham, Mass.) to remove excess Alexa 488 dye, viruses were checked by HA assay and then bound to glycan array. Labeled viruses were incubated on glycan microarray at 4° C. for 1 h, washed, and centrifuged briefly before being scanned with an InnoScan 1100 AL Mircroarray Scanner (Inopsys, Toulouse, France).

Viruses-Glycan Receptor Binding Assay.

Two biotinlyated glycan analogs, carbohydrates 3'-sialyl-N-acetyllactosamnine (3'SLN) representing SA2,3GA and 6'-sialyl-N-acetyllactosamine (6'SLN) representing SA2, 6GA, were purchased from GlycoTech (Gaithersburg, Md.). The glycan stocks were reconstituted at 1 mg/ml in 50% glycerol—PBS (vol/vol) solution according to the manufacturer's instructions and were stored at 4° C. until use. The viral particles in wild-type reassortant virus bearing HA161Y (rg-wt) and a mutant virus bearing $HA_{161F}$ (rg-Y161F) were determined using a Virocyt 2100 virus counter (ViroCyt, Boulder, Colo.). The kinetics buffer (PBS pH 7.4 with 0.01% bovine serum albumin and 0.002% Tween-20) containing neuraminidase inhibitors (10 μM zanamivir hydrate and 20 μM oseltamivir phosphate) was used to titrate the biotinylated glycan analogs and viruses during the binding assay (Xiong et al., 2013). Binding of viruses (at 1 μM/virus) to the biotinylated glycan analogs was performed in an Octet RED96 biolayer interferometer equipped with streptavidin biosensor tips (PALL FortéBIO, Menlo Park, Calif.) according to the manufacturer's assay protocol: 1) Biosensor coating with biotinylated glycan analogs×300 sec; 2) Virus association×1,200 sec; and 3) Dissociation in the kinetics buffer with neuraminidase inhibitors×1,000 sec. The entire measurement cycle was maintained at 30° C. with orbital shaking at 1,000 rpm.

Analyses of Virus Thermostability.

Purified viruses were diluted in PBS to 128 HAU, and dispensed by 120 μl into 0.2-ml, thin-walled PCR tubes (USA Scientific, Ocala, Fla.). Tubes were placed in a Gradient Veriti 96-Well Thermal Cycler #9902 (Life Technologies, Camarillo, Calif.). The temperature range was set at 51.5°-63.0° C. Tubes were heated for 40 min, then transferred to ice. Control samples containing 120 μL of virus were incubated for 40 min at 0° C. Virus content in each sample was determined by HA assay using a 0.5% suspension of turkey erythrocytes. Each virus sample was analyzed three times for thermostability.

Animal Experiments.

Two groups of 6-week-old female BALB/c mice (Harlan Laboratories, Indianapolis, Ind.) were intramuscularly inoculated with 15 μg (in a 50-μl volume) of a formaldehyde-inactivated vaccine candidate or wild-type virus (n=10 mice/group). Two weeks later, a booster vaccine was administered with the same amount of immunogen. A group of mock-vaccinated mice (n=10) received an equal volume of PBS. A group of mice serving as environmental controls (n=5), were not vaccinated or challenged. Two weeks after daily monitoring the booster vaccination, mice were anesthetized and challenged by intranasal inoculation with mouse-adapted CA/04 at 10 times the 50% lethal dose. Serum samples were collected from mice before challenge and tested by HI assays. To determine lung virus titers, five mice were euthanized at day 4 after challenge. Lungs (n=3) were homogenized and resuspended in 1 ml of sterile PBS, and virus titers were determined in MDCK cells. The lung samples were also fixed in formalin and stained with hematoxylin and eosin stain for pathologic examination. Clinical signs, survival rate, and body weight of the remaining mice (n=5) were monitored for 14 days after challenge.

Biosafety and Animal Handling.

All laboratory and animal experiments were conducted under BSL-2 conditions, with investigators wearing appropriate protective equipment, and in compliance with protocols approved by the Institutional Animal Care and Use Committee of Mississippi State University.

Structural Modeling.

Crystal structures of the HA protein of the A(H1N1) pdm09 virus and the binding sites of 6'SLN and 3'SLN to this protein were obtained from PDB (Protein Databank: accession numbers 3LZG, 3UBN, and 3UBQ, respectively). Structural simulation of amino acid mutations was performed on the HA by using the computer algorithm FoldX with its empirical force field with crystal waters under the following conditions: temperature of 298K, pH 7, 0.05 ion strength. The binding structures and measure of contact distances were visualized by using Chimera. PoseScore, which was designed for ranking near-native ligand-protein interacting structures, was used to estimate the likeness of the protein-glycan binding avidities of the wild-type and mutant viruses to that of the native virus. Typically, PoseScore scores typically range from −100 to 100; the lower the score, the lower the binding affinity. The computational analysis of the effect of mutation on HA-glycan bindings was focused on the mutants with 161 (H3 numbering) location.

Genomic Sequences, Molecular Characterization, and Statistical Analyses.

HA sequences of IAVs were downloaded from the database of the Influenza Virus Resource on Jan. 30, 2017. Multiple sequence alignments were conducted by using MUSCLE software (Edgar, 2004). The mutations were identified by using Bioedit software (Hall, 1999). Survival curves were calculated by the Kaplan-Meier method, and significance was analyzed with the log-rank test using Graphpad Prism 5 software.

Results

Generation of RBS Variants of CA/04 and Assessment of their Growth Characteristics in Cells.

To identify mutations associated with high-yields of CA/04/PR8 reassortant viruses, a cDNA library carrying random mutations in the CA/04 HA RBS was generated by epPCR and screened by Sanger sequencing. Hereafter, the term rg is used to refer to mutants from epPCR. For example, rg-Yb161F denotes a reassortant virus from epPCR with a Y161F mutation. Each mutated plasmid, together with the neuraminidase plasmid of CA/04 and internal genes (PB2, PB1, PA, NP, M, NS) plasmids of PR8, was used to rescue virus by a reverse genetics approach. As a result, I obtained a total of eight mutants; rg-D130E, rg-P140T, rg-L154F-K156Q, rg-S160T, rg-Y161 F, rg-K174E rg-S188I, and rg-Y201H (Table 1).

TABLE 1

Characterization of MDCK cell grown receptor binding site mutants generated by error-prone PCR-based mutagenesis strategy

| | | | HA titers[d] | | | | |
|---|---|---|---|---|---|---|---|
| Mutation[a] | HI[b] | $TCID_{50}$[c] | Guinea | Chicke | Horse | Turkey | Dog[e] |
| rg-wt | 640 | 5.749 | 4 | 8 | <2 | 16 | 8 |
| P140T | 640 | 5.91± | 4 | 4 | <2 | 32 | 4 |
| S188I | 640 | 5.91± | 4 | 16 | <2 | 16 | 4 |
| S160T | 320 | 6.08± | 4 | 2 | <2 | 16 | 8 |
| Y201H | 320 | 6.08± | 16 | 8 | <2 | 64 | 16 |
| D130E | 320 | 6.249 | 16 | 16 | <2 | 128 | 32 |
| K174E | 320 | 6.249 | 16 | 16 | <2 | 64 | 32 |
| L154F- | 640 | 6.249 | 16 | 4 | <2 | 128 | 64 |
| Y161F | 640 | 8.249 | 256 | 1,024 | <2 | 512 | 128 |

[a]Viruses that carry mutations at the receptor binding site of wild-type influenza A/California/04/09 (H1N1) virus (CA/04) were generated by using an error-prone-based reverse genetic system. rg-wt, CA/04 mutant.
[b]HI, hemagglutination inhibition. Titers were determined by using ferret serum (anti-CA/04).
[c]$TCID_{50}$, 50% tissue culture infectious dose. The virus titers were determined by $TCID_{50}$ assay in MDCK cells.
[d]HA, hemagglutination assays against types of red blood cells were performed using standard procedures.
[e]Beagle.

Analysis of viral growth kinetics showed that replication efficiencies of these 8 mutants varied greatly in MDCK cells. Among the mutants, rg-D130E, rg-K174E, rg-L154F-K156Q, and rg-Y161F increased virus titers compared with the wild-type reassortant virus rg-wt. Mutants rg-S160T, rg-P140T, rg-S1881, and rgY201H grew to similar titers as did rg-wt (Table 1). Among all mutants, rg-Y161F had the highest virus titer at 8.249 log (50% tissue culture infectious dose [TCID50]), which was >300-fold higher than that of the wild-type virus in MDCK cells.

To determine if the mutations at the RBS altered HA antigenicity, the panel of eight RBS CA/04 mutants was subjected to a hemagglutination inhibition (HI) assay, using ferret antisera against CA/04. The HI titers of four reverse genetic variants, rg-Y161F, rg-L154F-K156Q, and rg-P140T, were equivalent to that of the rg-wt virus. The remaining four mutants, rg-D130E, rg-K174E, rg-S160T, and rg-Y201H, had 2-fold lower HI titers compared with that of the rg-wt. Thus, all of the RBS mutants were antigenically similar to the parental CA/04 virus despite the presence of an altered virus growth property. Due to its preferred growth and unaltered antigenic characteristics, rg-Y161F was selected as a candidate vaccine virus for further studies.

Figure 1B:
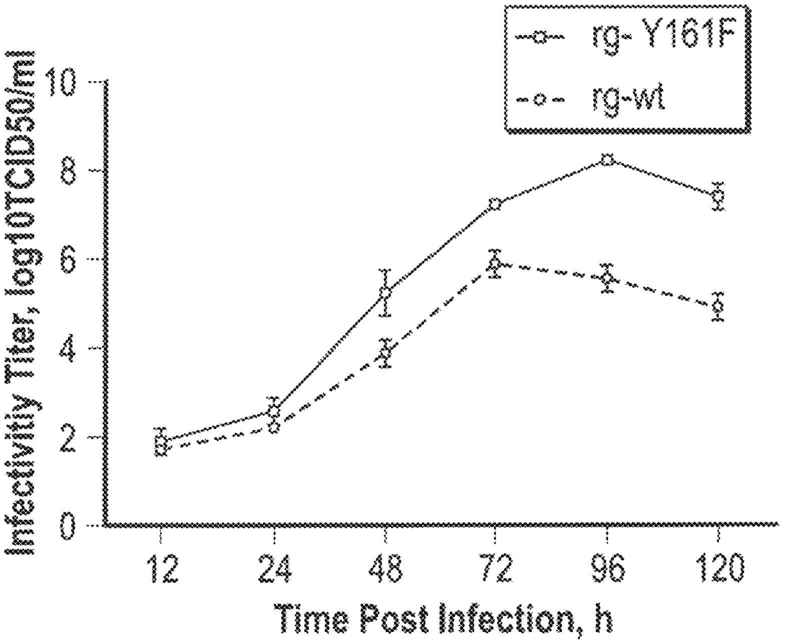
Figure 1C:
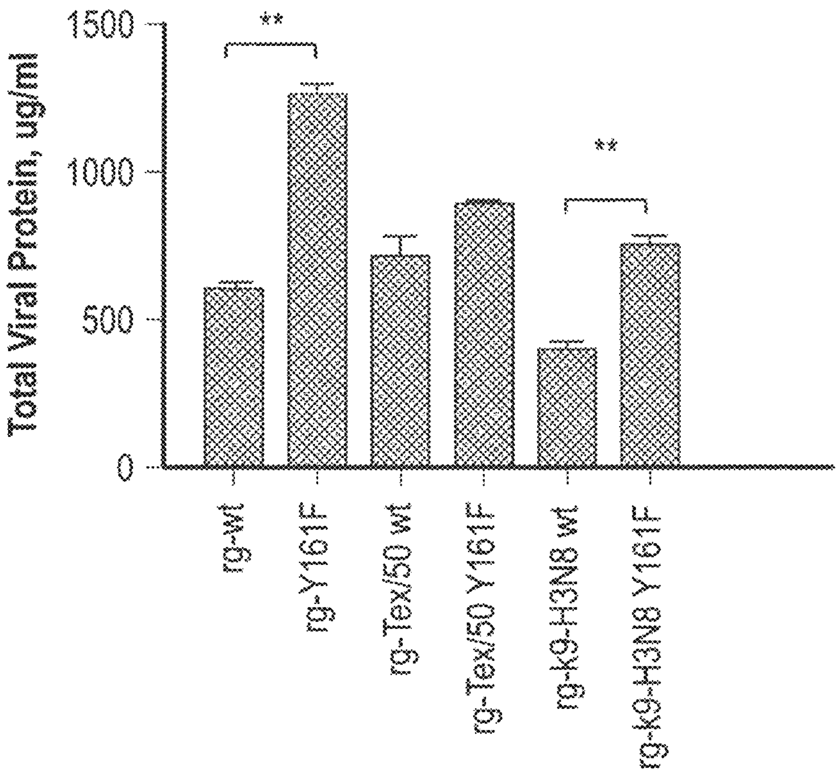

Growth properties of rg-Y161F. To evaluate the replication efficiencies of rg-Y161F, its growth kinetics alongside were characterized rg-wt in MDCK and Vero cells. I infected cells with viruses at a multiplicity of infection (MOI) of 0.001 (MDCK cell infection) or 0.01 (Vero cell infection) and determined the growth kinetics of the viruses for up to 96 h in MDCK cells and 120 h in Vero cells. In MDCK cells, the virus titers of rg-Y161F reached $10^{8.66}$ $TCID_{50}$/ml at 72 b after infections, >300-fold higher than the highest virus titer from rg-wt, as shown in FIG. 1A. In Vero cells, the titers of rg-Y161F reached $10^{8.25}$ $TCID_{50}$/ml at 96 h after infections, a titer>100-fold higher than the highest virus titer from rg-wt, as shown in FIG. 1B. The total viral protein of rg-Y161F in cells reached a mean titer of 1236.2 μg/ml, 2.07-fold higher than that of wild-type CA/04 (p=0.008), as shown in FIG. 1C. These results show that mutation Y161F facilitates the replication efficiency of CA/04 in MDCK and Vero cells.

Impact of HA RBS mutations on virus binding to erythrocytes. Possible mechanisms for the increased yields of rg-Y161F were explored by examining its interaction with host receptors. Due to their unique glycan receptor profiles (i.e., types and distributions of alpha-2,3-linked sialic acid on galactose [SA2,3GA] and alpha-2,3-linked sialic acid on galactose [SA2,6GA]), erythrocytes from various hosts have often been used to characterize receptor binding properties for influenza viruses through hemagglutination assays (HA assays). Erythrocytes from guinea pig, chicken, horse, turkey, and dog (beagle) were used to compare the glycan profiles of the full panel of eight mutants. As shown in Table 1, all mutants and the wild-type (rg-wt) virus agglutinated erythrocytes from guinea pig, chicken, turkey, and beagle to different extents, but they did not agglutinate those from horse. The eight mutants could be separated into three groups: 1) those with increased HA, titer against guinea pig, chicken, turkey, and beagle erythrocytes (rg-D130E, rg-K174E, and rg-Y161F mutants); 2) those with an hemagglutination pattern similar to that for wild-type virus (rg-S160T; rg-P140T, and rgS188I mutants); and 3) those that had increased HA titer against guinea pig, turkey, and beagle erythrocytes but no change in HA titers against chicken erythrocytes (rg-L154F-K156Q and rg-Y201H mutants). Among the eight mutants, it was striking that rg-Y161F had the highest HA titers (range, 128-1,024 HA units (HAU) to erythrocytes from guinea pig, chicken, turkey, and beagle.

Effect of Y161F Mutation on the Receptor Binding.

Figure 2:
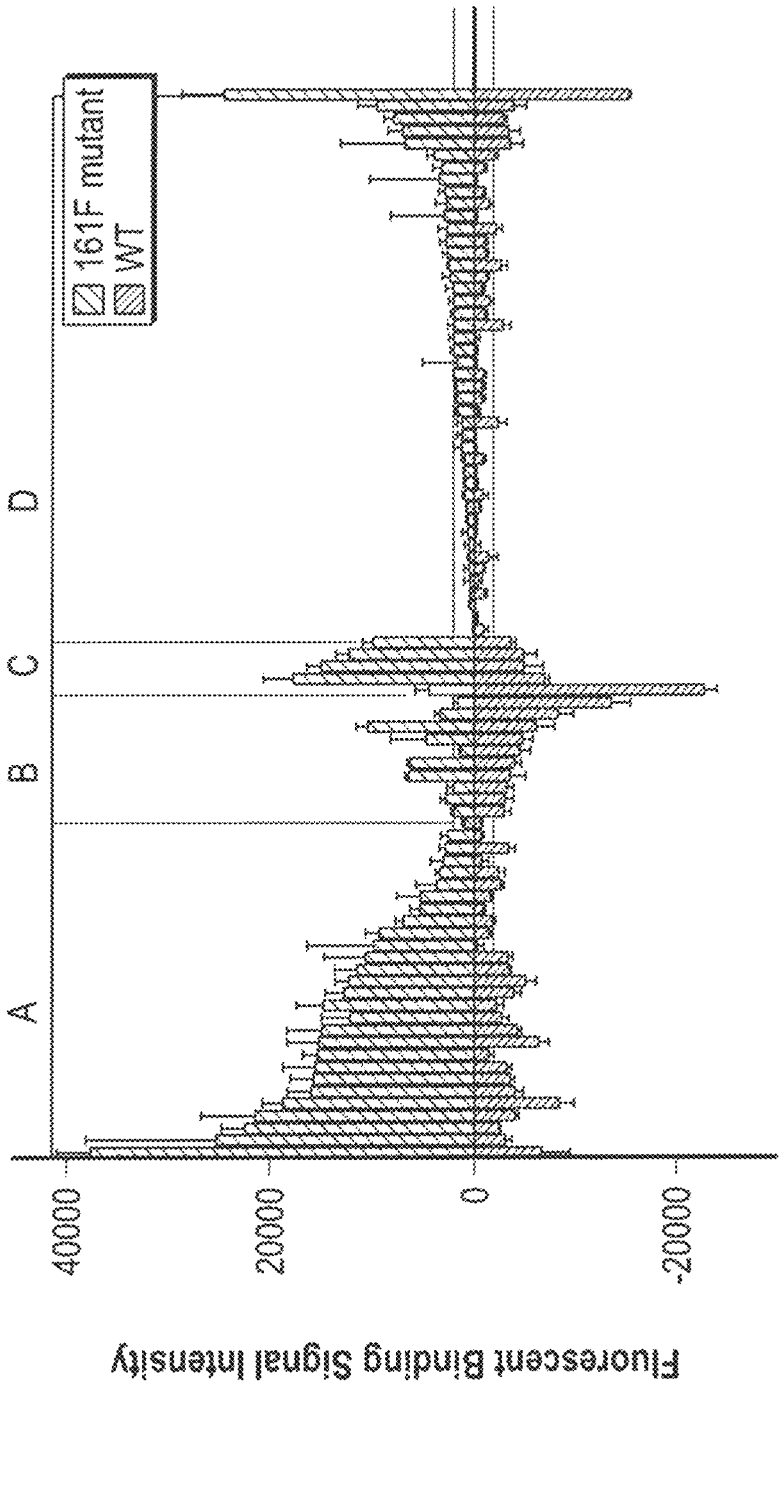
FIG. 2 depicts a glycan microarray showing receptor binding specificity of wild-type and Y161F hemagglutinin 1 mutant viruses analyzed by glycan microarray analysis. A-D represent different categories of glycans: A, alpha-2,3 sialic acid glycans; B, alpha-2,6 sialic acid glycans; C, alpha-2,3 and alpha-2,6 acid glycans; D, non-sialic acid glycans. Vertical bars denote the fluorescent binding signal intensity.
Figure 6:
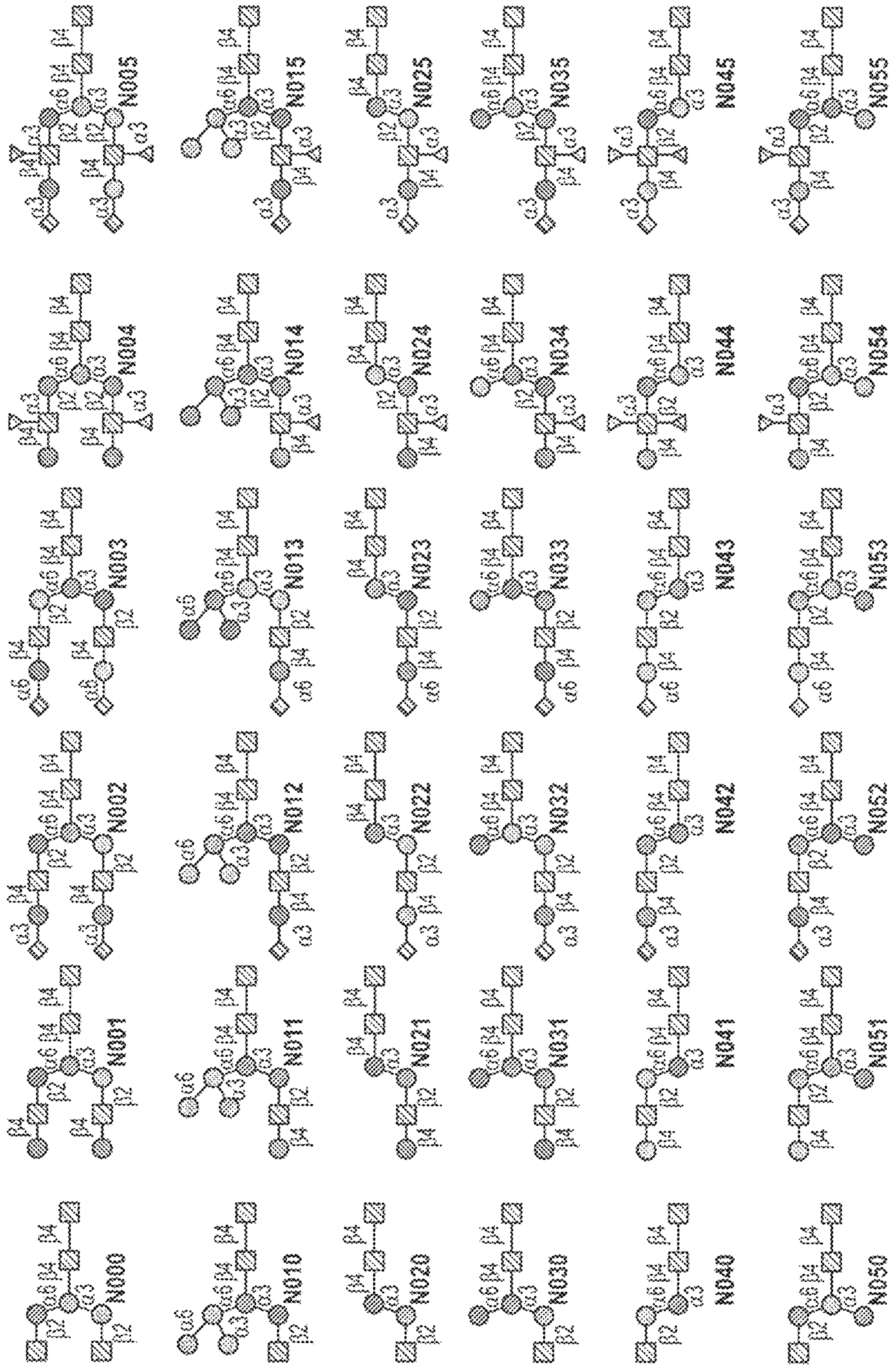
FIG. 6 depicts structures of chemoenzymatically synthesized N-linked glycans on the isoformer microarray.
Figure 6:
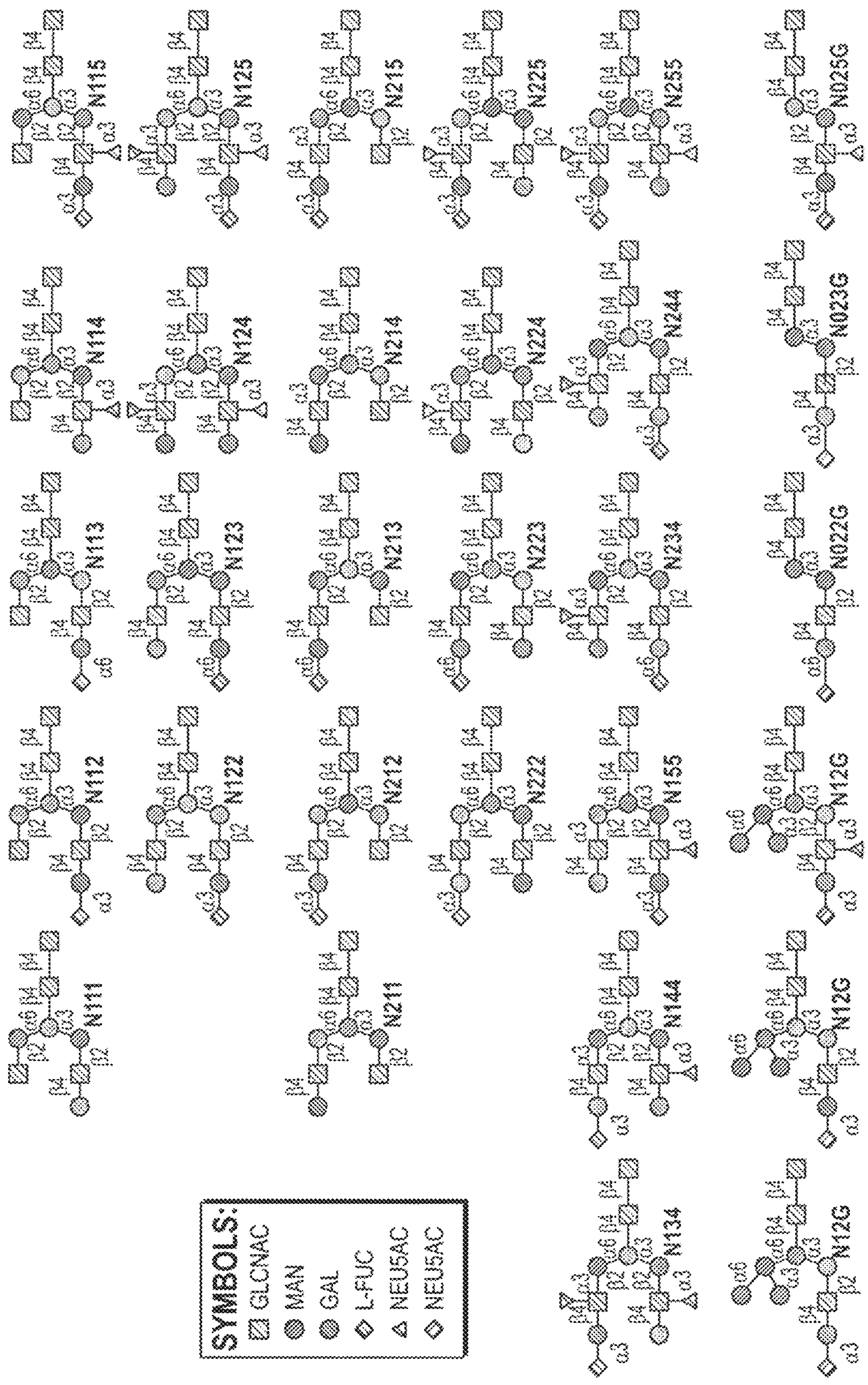

To further explore the molecular mechanisms of the rg-Y161F high-growth yield phenotype, its receptor binding profile was characterized by using an N-linked glycan isoformer microarray. The microarray consisted of 66 chemoenzymatically synthesized and purified N-glycans (Li et al., 2015), as shown in FIG. 6 and FIG. 7. As shown in FIG. 2, both rg-wt and rg-Y161F bound predominantly to N-glycans terminating with Neu5Ac. The rg-wt virus showed binding to 2,6-Neu5Ac-linked glycans (N0x3, N113, NN144, N213, N223, and N244), whereas the Y161F mutant showed a preference for binding to α2,3-Neu5Ac-linked glycans (N0x2, N112, N122, N134, N212, N222, N234, N0x5, N115, N125, N155, N215, N225, and N255) and relatively weaker binding to α2,6-Neu5Ac-linked glycans. Neither rg-wt or rg-Y161F were observed with noticeable binding toward 2,6-Neu5Gc-terminated glycans (N013G and N023G) or α2,3-Neu5Gc-terminated glycans (N012G, N022G, N015G, and N025G).

Figure 3A:
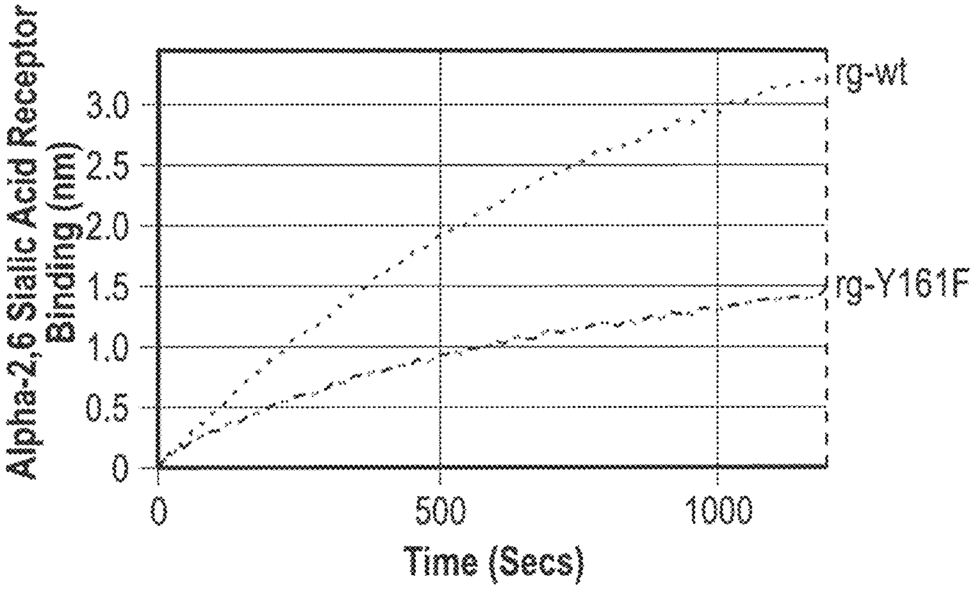
FIG. 3A-3G depict glycan binding specificity of virus by Bio-Layer Interferometry (fortéBIO, Menlo Park, Calif.). Individually.
Figure 3B:
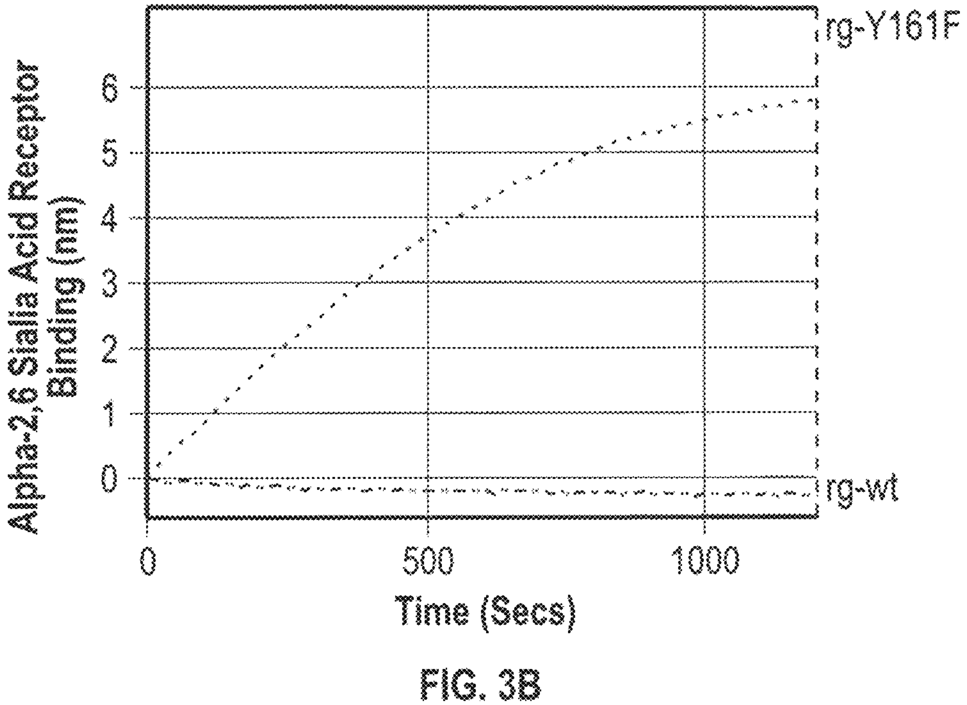
Figure 3C:
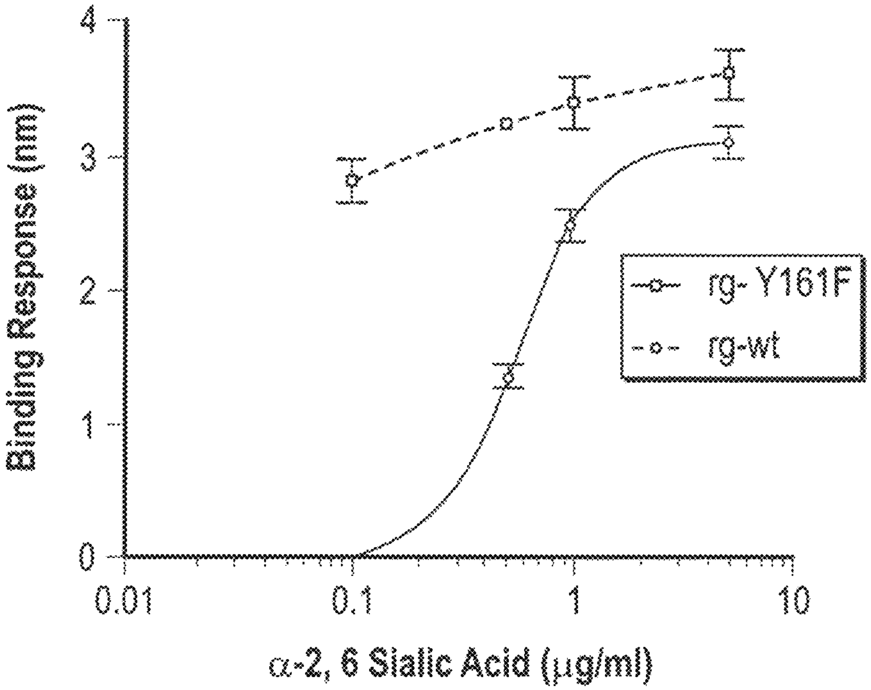
Figure 3D:
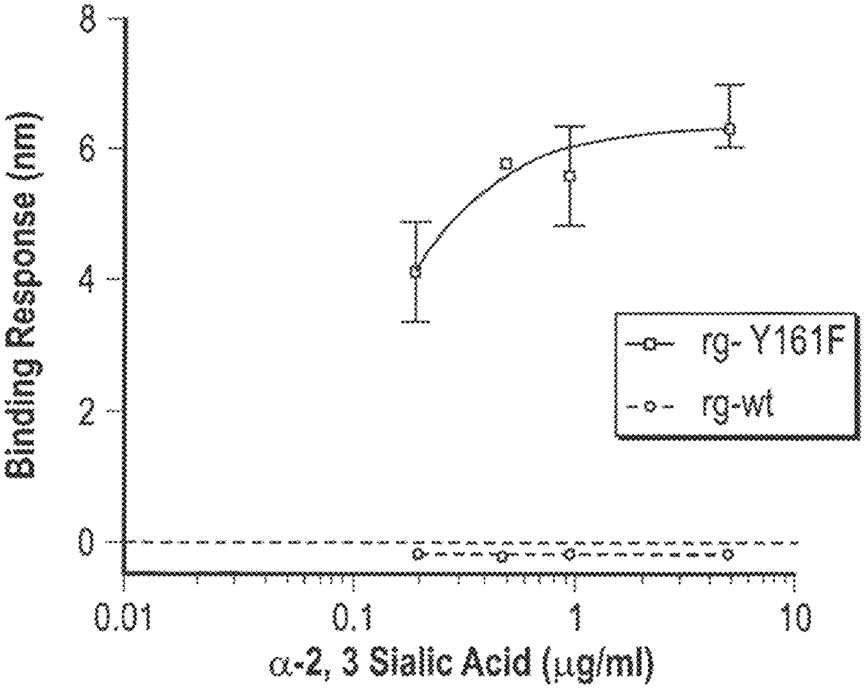

To confirm the binding profiles revealed by glycan array, glycan binding assays were performed to characterize the dynamics and avidity of virus binding to two glycan analogs, 3'SLN and 6'SLN. The representative binding plots for each glycan analog are shown in FIGS. 3A and 3B. Both rg-wt and rg-Y161F showed strong binding to 6'SLN, although rg-Y161F exhibited relatively weaker binding affinity than rg-wt (<1.2 fold, FIG. 38). Conversely, rg-Y161F showed much stronger binding to 3'SLN; whereas rg-wt had no detectable binding at the same 3'SLN concentration range tested, as shown in FIG. 3D. These results confirmed the glycan array profiles that the Y161F mutation in HA dramatically increased binding affinity to 3'SLN while retaining strong binding affinity to 6'SLN.

Structural Mechanism of Increased Rg-Y161F Binding to 3'SLN and 6'SLN.

Figure 3E:
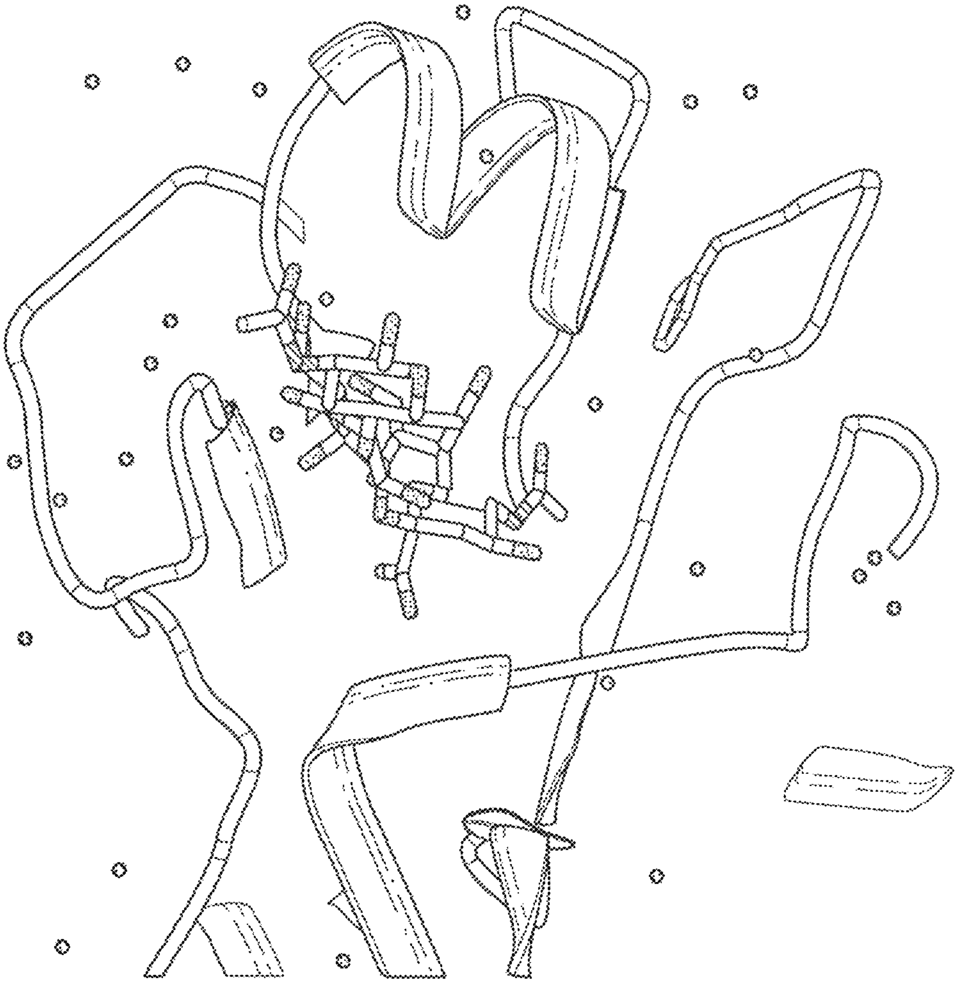
Figures 3F, 3G:
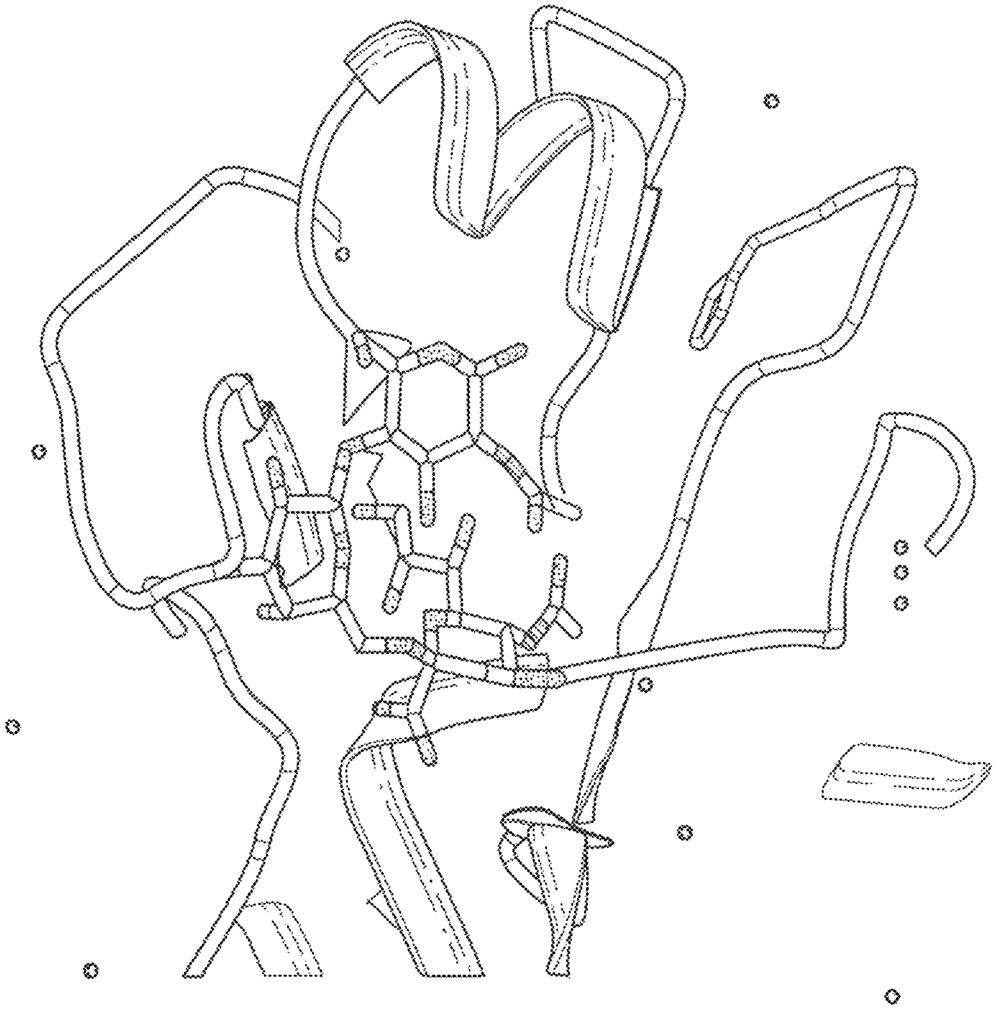

Crystal structure modeling was performed to characterize the effect of the Y161F mutation on binding affinity between HA and two testing glycan analogs, 3'SLN, as shown in FIG. 3E, and 6'SLN, as shown in FIG. 3F. For 3'SLN, the PoseScore of the wild-type CA/04 HA was 5.99, whereas that for the Y161F HA was −6.63. For 6'SLN, the PoseScores for wild-type CA/04 HA and the Y161F mutant were 2.06 and −11.89, respectively, as shown in FIG. 3G. These results show that the Y161F mutation leads to increased binding of CA/04 to 3'SLN and 6'SLN.

Effect of the Y161F Mutation on Replication of Other IAVs.

Figure 4B:
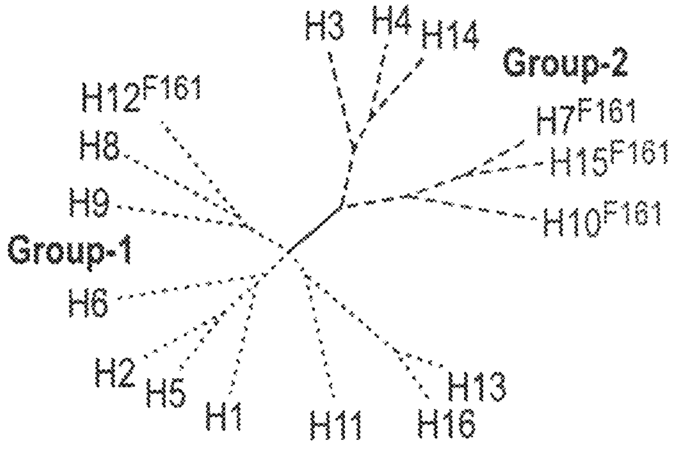

To understand the naturally occurring molecular polymorphisms at residue 161 of HA, a total of 59,016 HA sequences covering all 18 documented HA subtypes (H1-H18) of IAVs were compared. The results show that Y161 is conserved in H1-H5, H8, 9, H11, H13, H14, and H16 IAV subtypes, whereas F161 is conserved in H7, H10, H12, and H15 IAV subtypes, as shown in FIG. 4A. Phylogenetically, H7, H10, and H15 are group 2 HAs, and H15 is a group 1 HA, as shown in FIG. 4B.

To test whether the Y161F mutation would increase growth yields in IAVs other than CA/04, I generated 161F mutants for two additional strains: TX/50 and k9-H3N8. Analysis of growth kinetics in MDCK cells at an MOI of 0.001 showed that the TX/50 161F mutant generated viral titers of $10^{3.17}$, $10^{5.92}$, $10^{7.20}$, and $10^{7.00o}$ $TCID_{50}$/ml at 12, 24, 48, and 72 h, respectively. This finding compared with $10^{2.33}$, $10^{5.25}$, $10^{7.08}$, and $10^{7.00o}$ $TCID_{50}$/ml at 12, 24, 48, and 72 h, respectively, for the wild type TX/50 virus. The TX/50 161F mutant in MDCK cells generated a mean total viral protein titer of 882.2 μg/ml, 1.15-fold higher than that for CA/04 wild-type virus, as shown in FIG. 1C. When subjected to ferret antisera in an HI assay, the TX/50 wild-type virus and 161F mutant both had mean HI titers of 1:1280.

Figure 4C:
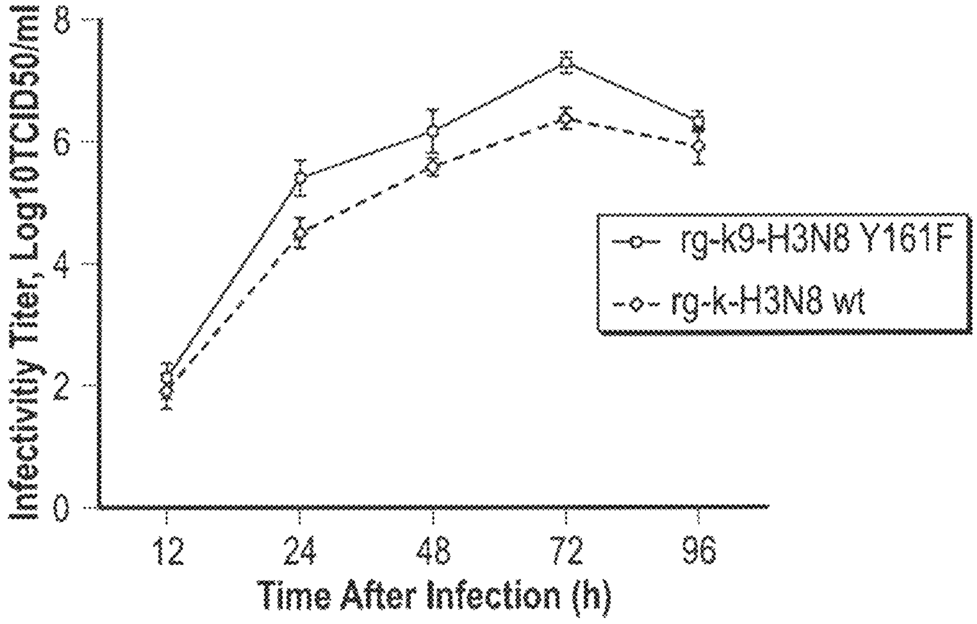
Figure 4D:
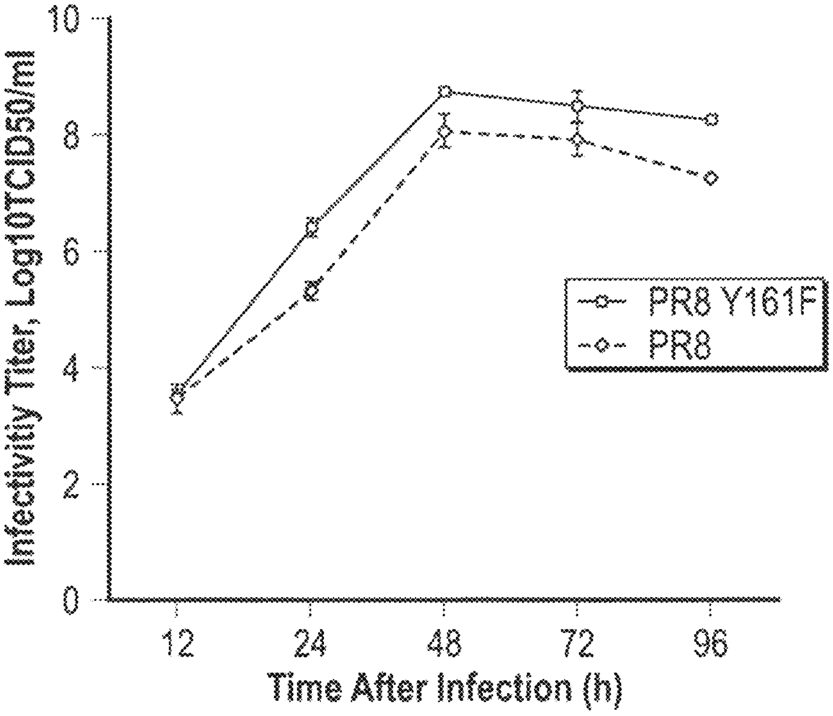

Analysis of growth kinetics in MDCK cells at an MOI of 0.001 showed that the 161F mutant of k9-H3N8 had the highest titer ($10^{7.249}$ $TCID_{50}$/ml) at 72 h after infection; this titer was about 10-fold higher than that generated by the k9-H3N8 wild-type virus, as shown in FIG. 4C. The mean HI titers of wt and rg k9-H3N8 to ferret antisera was 640 and 533, respectively. The total viral protein of the k9-H3N8 161F mutant reached a mean titer of 777.2 μg/ml, which was 1.85-fold higher than that of k9-H3N8 wild-type virus (p=0.02), as shown in FIG. 1C.

The results show that the Y161F mutant enhances replication efficiency but does not change the antigenicity of TX/12 and k9-H3N8 viruses.

Effect of the Y161F Mutation on Replication Efficiency of IAVs in Eggs.

Figure 1D:
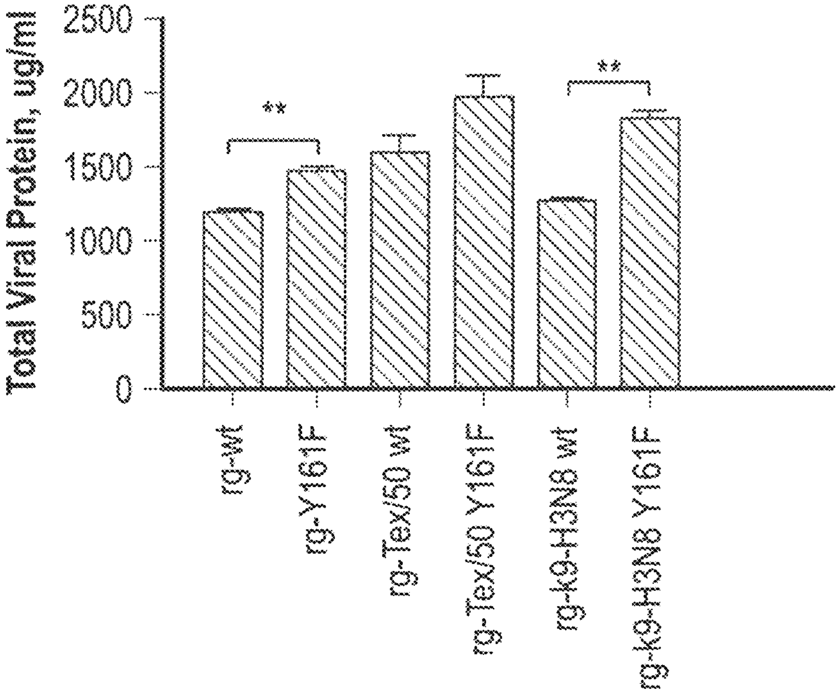

While an elevated growth phenotype of HAY161F containing viruses in cells was shown, its impact on egg growth was next determined. This was done by quantifying the total protein yields of wt and Y161F mutant H1N1, H3N2, and H3N8 IAVs in eggs. The total viral protein of the rg-Y161F mutant reached a mean titer of 1,460.2 μg/ml, 1.22-fold higher than that of wild-type CA/04. Similarly, for TX/50, the Y161F mutation conferred a 1.23-fold increase in total viral protein (1,589.2 μg/ml). The total viral protein of the k9-H3N8 Y161F mutant reached a mean titer of 1,824.2 μg/ml, 1.45 fold higher than that of wild-type k9-H3N8, as shown in FIG. 1D. Thus, the Y161F mutation also increased viral replication efficiency of three H1N1, H3N2, and H3N8 IAVs tested in eggs.

Impact of the Y161F Mutation on Viral Thermostability.

Figure 4E:
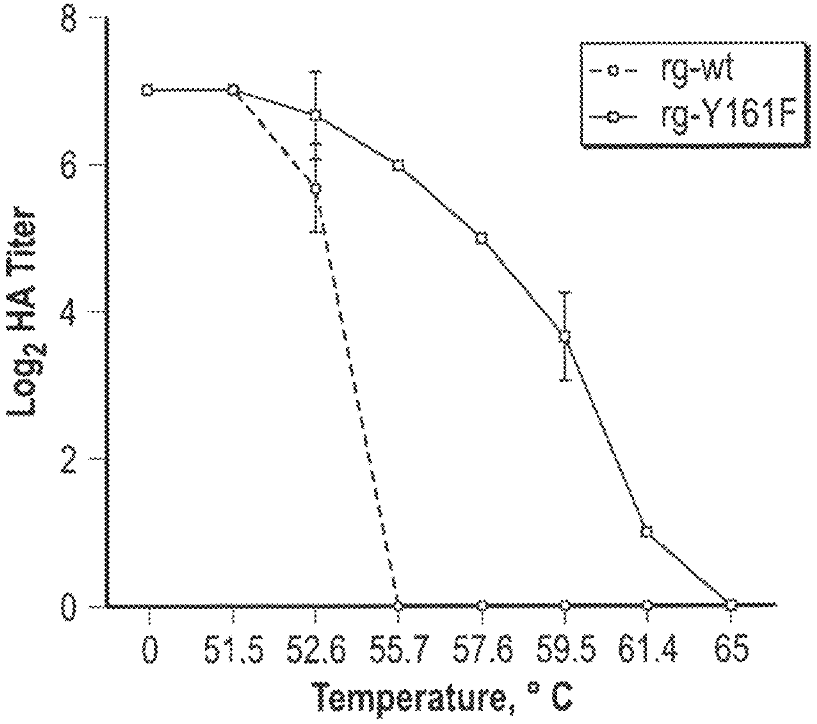
Figure 4F:
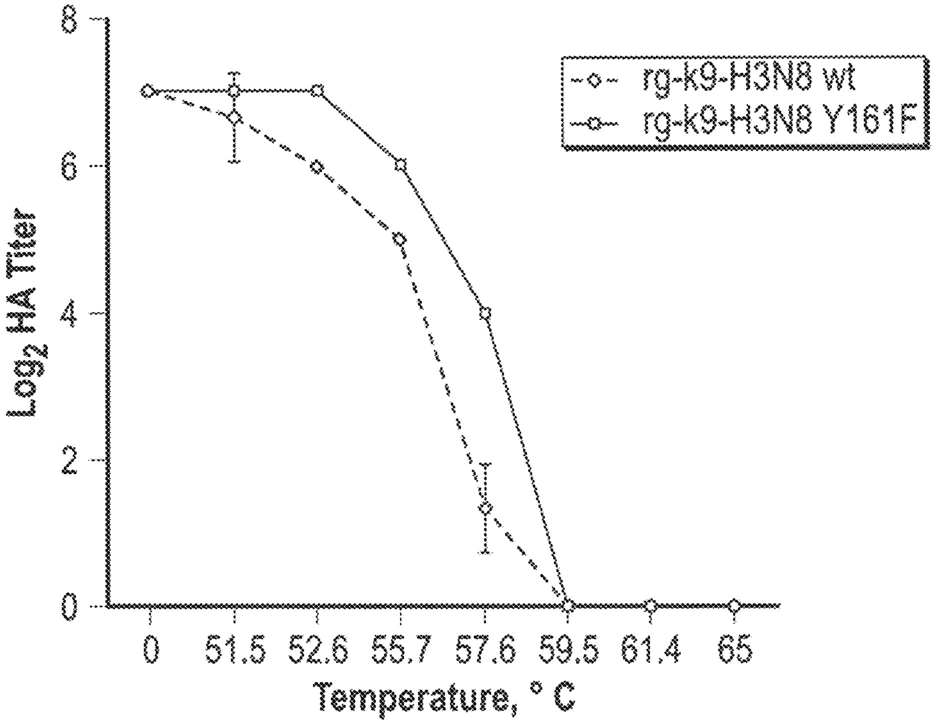

Another desirable property of an influenza vaccine virus is an increased stability. To determine whether the Y161F mutation correlated with changes in viral thermostability, purified viruses were diluted to 128 HAU/50 μl and incubated at a series of high temperatures (51.5°-65° C.) for 40 min, and the integrity of the HA protein was then detected by an HA assay using 0.5% turkey erythrocytes. The CA/04 rg-wt virus showed a precipitous drop in HA titer (from 128 to 2 HAUs) after 40 min of incubation at 55.7° C. In contrast, rg-Y161F maintained an HA titer of 64 HAU at 55.7° C. which did not drop until 59.5° C. The mutant virus maintained an HA titer of 2 HAU even at 61.4° C. The rg-wt virus completely lost its hemagglutination ability at 55.7° C., as shown in FIG. 4E. Similar phenotypes were observed in the 161F mutants for k-H3N8. The k9-H3N8 Y161F mutant had an HA titer of 16 HAU when incubated at 57.6° C. for 40 min; this titer was 8-fold higher than that of wild-type H3N8 virus, as shown in FIG. 4F. For TX/50, the wild-type and Y161F viruses maintained titers of 8 HAU and 16 HAU, respectively, at 61.4° C. (data not shown). Taken together, the results show that the Y161F mutation conferred higher viral temperature stability on viruses.

High-Yield Vaccine Candidate Protected Mice Against Lethal Challenge.

Although I have shown that the Y161F mutation had no impact on HAI titers, it was confirmed that there was not an associated loss in vaccine efficacy. To do this, inactivated whole virus vaccines were prepared from rg-wt and rg-Y161F CA/04 viruses and evaluated their efficacy in a mouse model. Mice were administered vaccine or PBS (as a mock vaccine, and 2 weeks later blood samples for testing were collected. All vaccinated mice had seroconverted and their HI titers were substantially higher than those of the mock-vaccinated mice (Table 2); mice vaccinated with rg-wt vaccine and rg-Y161F vaccine had log 2(HI) titers of 7.65±0.57 and 7.32±0, respectively. The heterologous HI titers were indistinguishable (p=0.3739) from homologous titers, again demonstrating the antigenic similarly of wt and mutant viruses.

TABLE 2

Immunologic and pathogenic responses in mice challenged with mouse-adapted influenza A/California/04/09 (H1N1)

| Vaccine group | $Log_{10}TCID_{50}$/ml, mean ± SD[a] | $Log_2$HI titer, mean ± SD[b] | $log_2$HI titer, mean ± SD[c] |
|---|---|---|---|
| WT | Below detection limit | 7.65 ± 0.57 | 7.32 ± 0 |
| Mutant | Below detection limit | 7.32 ± 0 | 7.32 ± 0 |
| PBS[d] | 5.28 ± 0.14 | Below detection limit | Below detection limit |

[a]Groups of BALB/c mice were inoculated intranasally with 10% the 50% lethal dose of mouse-adapted CA/04 virus under light anesthesia. Three mice from each group were euthanized on day 4 after virus challenge, and virus titers in lungs were determined by $TCID_{50}$ (50% tissue culture infectious dose) in MDCK cells.

[b]Serum sample were collected before challenge, and antibody response levels against the wild-type (WT) virus were measured by using the hemagglutination inhibition (HI) assay.

[c]Serum samples were collected before challenge, and antibody response levels against the immunogen mutant were measured by using the HI assay.

[d]PBS, phosphate-buffered saline mick-infection

Figure 5A:
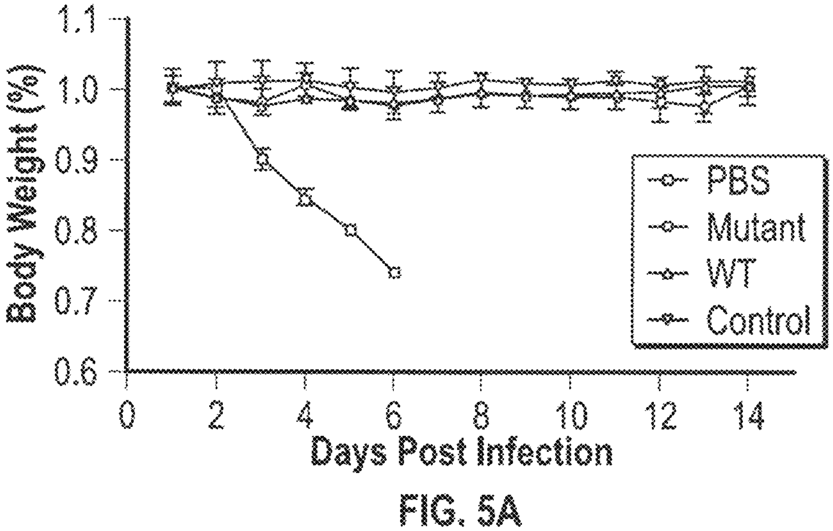
FIG. 5A-5F depict line graphs of weight loss and survival, among vaccinated mice challenged with a lethal dose (LD) of influenza A/California/04/09 (H1N1) virus (CA/04). Individually.
Figure 5B:
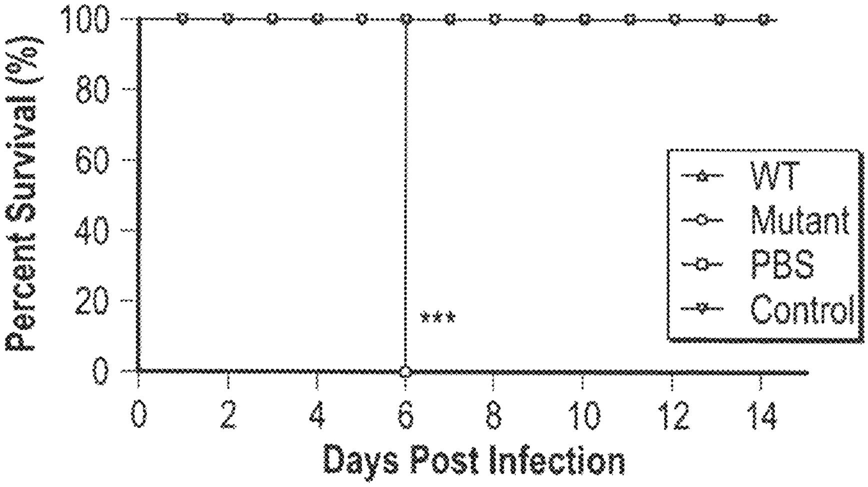

Following challenge, a high level of virus replication (up to $10^{5.45}$ $TCID_{50}$) was observed in mock-vaccinated mice, but no virus was detected in mice vaccinated with rg-wt or rg-Y161F derived vaccine. Mock-vaccinated mice exhibited signs of inactivity and lethargy, had ruffled hair, and rapidly lost weight following challenge, as shown in FIG. 5A. In contrast, mice vaccinated with rg-wt or rg-Y161F derived vaccines did not exhibit any detectable clinical signs. All vaccinated mice survived, but by post-challenge day 6, all mock-vaccinated mice (n=5) had lost 25% of their pre-experiment body weight and were euthanized, as shown in FIG. 5B.

Figure 5C:
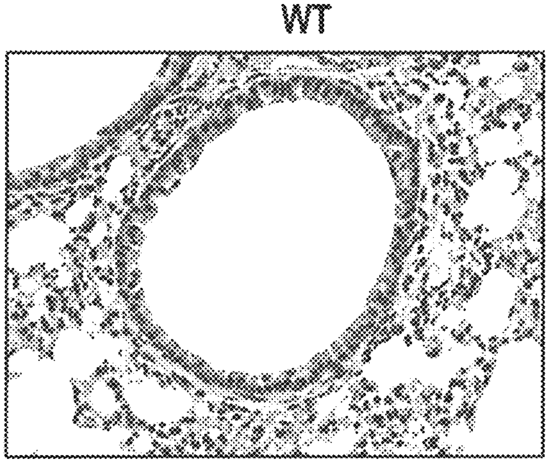
Figure 5D:
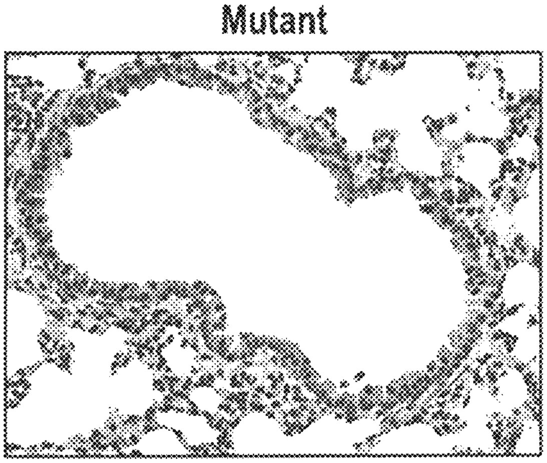
Figure 5E:
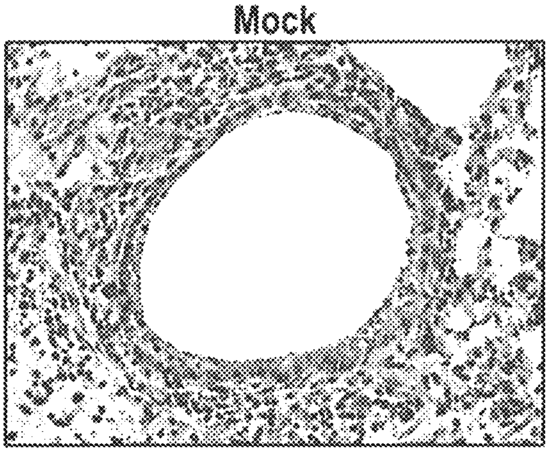
Figure 5F:
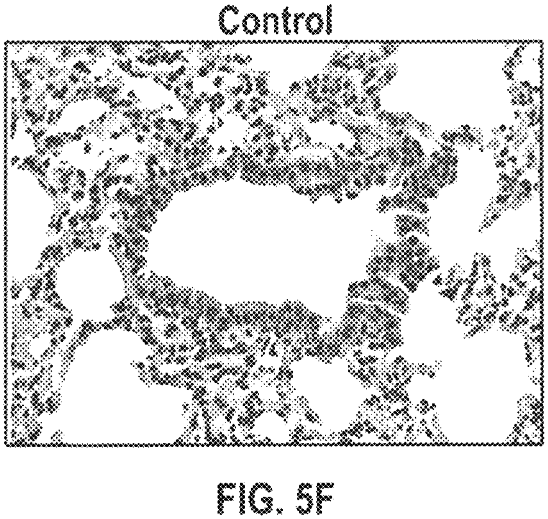

Results from histopathologic analyses showed that mice immunized with rg-wt or rg-Y161F derived vaccine had no apparent pathologic changes, as shown in FIGS. 5C and 5D. However, the mock-vaccinated mice exhibited severe bronchiolitis, and their bronchioles showed necrosis and some attenuated regenerative epithelial cells along the basement membrane, as shown in FIG. 5E.

In summary, the results from experiments in mice suggest that the Y161F mutation in HA did not alter the viral antigenicity of CA/04 or efficiency of the vaccine in mice.

DISCUSSION

An effective influenza vaccination is dependent on a number of factors, not the least of which are high yielding and stable vaccine viruses. A high yield of virus is critical to vaccine manufacturing, and thermostability of viral antigens is critical for vaccine shelf life which can be compromised during transportation and storage. In this study group of randomly generated CA/04 mutants carrying substitutions at the HA RBS were screened. While a number of these mutants displayed enhanced features, one, containing an Y161F change, had increased thermostability and the highest viral yields. This mutation was also able to impart these properties on a seasonal H3N2 and a canine H3N8 virus showing that the effect was not subtype-specific. Furthermore, the Y161F mutation did not change the antigenicity of the H1N1, H3N2, and H3N8 viruses tested. Animal experiments further showed that the Y161F change in CA/04 did not have measurable impact on the efficacy of inactivated whole-virus vaccines containing it. These results highlight the application potential of the HA 161F signature in influenza vaccine manufacture.

The initial step in viral infection is the binding of HA to the sialic acid receptors on the epithelial cell surface (Skehel et al., 2000). This interaction is mediated by the RBS which is located at the globular head of the HA and consists of the 130 and 220 loops and the 190 helix. Mutations at the RBS have long been known to affect the yield of a vaccine strain which was my rationale for targeting it. For example, mutation L194P increased the yield of an A/England/611/07 (H3N2) 6+2 reassortant virus (Hartgroves et al., 2010), and single or double mutations at 191 (194 in 13), 197 (200), 222 (225), and 223 (226) increased replication of A/California/7/09 (H1N1) in eggs (Chen et al., 2010). Mutations at residue 186 and 194 in the HA of an A(H1N1)pdm09 virus have also been shown to improve viral titers in MDCK cells and eggs (Suphaphiphat et al., 2009). Avian virus yields can also be improved by targeting the RBS and the double mutation of N133D/G198E in the HA have been reported to increase H7N9 viral yields (Chen et al., 2014). The challenge of targeting the RBS for improving virus yields is that some mutations which lead to improved growth also alter antigenicity. For example, mutation G144E was shown to increase the yield of B/Victoria/504/2000, but the antigenic properties of the virus were also changed (Lugovstev et al., 2005). Single amino acid changes at positions 119 (122 in H3), 153 (156), 154 (157), and 186 (189) could increase the yield of A/California/7/09 (H1N1) in eggs, but mutations at residues 153 (156 in H3), 154 (157), and 155 (158) drastically altered viral antigenicity (Robertson et al., 1836-1843).

The natural plasticity of the RBS for accepting substitutions was highlighted by Yasugi et al. (Yasugi et al., 2009). These authors used Roche 454 sequencing to directly sequence nasal specimens from three patients infected with A(H1N1)pdm09 virus. They found the virus' HAs showed high levels of amino acid diversity, with polymorphisms ranging from 3.45-8.59% for a K119N substitution, 1.01-4.99% for a N125D substitution, 0.74-21.49% for a D222G substitution, and 2.39-4.64% for a Q223R substitution (Yasugi at al., 2009). The percentages of the K119N, N125D, D222G, and Q223R mutations reached up to 60.4%, 96.7%, 85%, and 95.8%, respectively, after egg adaptation of the primary specimens (Yasugi et al., 2009). Similarly, mutations K119N and D222G were also found in the high-yield, egg-adapted A(H1N1)pdm09 virus vaccine strain NIBRG-121xp, and a Q223R mutation was found in another high-yield, egg-adapted A(H1N1)pdm09 strain NYMC-181A (Robertson et al, 1836-1843). These findings demonstrate that selection or generation of an HA variant, especially in RBS of HA, can in some cases be rapidly achieved. However, the genetic features for high-yield property are still not fully understood and generation of high-yielding viruses using classical virologic techniques is sometimes more challenging, in this study a random mutagenesis approach was opted for which generated eight mutants, of which four (D130E, K174F, L154F-K156Q, Y161F) increased viral yields in cells without changing antigenic properties (Table 1). Among these mutants, Y161F had the largest increase in viral replication efficiencies in both MDCK and Vero cells, as shown in FIG. 1A-1D. This invention also contemplates use of the mutant Y161F in egg production.

Binding to the host cell is the first step of influenza virus infection. Thus, the presence of favorable receptors on a specific cell is one of the key factors determining host and tissue tropisms of IAV. Most studies related to influenza receptors have classified the sialic acid receptors into two groups on the basis of positions of the sialic acid-galactose linkage: SA2,3GA or SA2,6GA. Both SA2,3GA and SA2,6GA are present in any single cell type, but their distributions varies based on the types of cells. For example, SA2,3GA and SA2,6GA are present in both MDCK and Vero cells, but SA2,3GA is considerably more abundant than SA2,6GA in both cell lines (Govorkova et al., 1996; Ito et al.; 1997, Seo at al., 2001). However, in chicken erythrocytes, SA2,6GA is more abundant than SA2,3GA (Aich et al., 2011). Thus, an ideal high-yield vaccine candidate would have high binding affinities to both SA2,3GA and SA2.6GA (Chen at al., 2012). This double binding was the phenotype the Y161F mutant in multiple assays, providing a plausible explanation for the increased yields in MDCK and Vero cells.

The HA RBS is a member of the lectin superfamily, and the specificity of RBS contributes to the host range of IAVs. Results of my structure modeling show that residue 161 locates at the top of the RBS, as shown in FIG. 3. Others have previously reported that an Y161A substitution in the H5N1 HA changed the receptor binding preference from Neu5Ac to N-glycolylneuraminic acid (Neu5Gc) (Wang et al., 2012). In addition, the Y161A mutants were best in viral replication and plaque forming ability. The binding preference of virus is changed by introducing the F substitution at residue 161. This substitution in CA/04 accommodates virus binding to both SA2,3GA and SA2,6GA and is responsible for the acquisition of specificity to SA2,3GA receptors. The Phe side chain lacks the $O^4$ hydroxyl group present on the Tyr shortening the distance between the oxygen atom of a water molecule and residue 161; and this facilitates acquisition of the viral specificity to SA2,3GA.

Environmental factors such as temperature and pH have been reported to affect airborne transmission of IAV, possibly by affecting viral thermostability (Pica et al., 2012). Thus, viral thermostability could affect the quality of and transmissibility of influenza viruses. A T3181 substitution in HA increased its stability and affected the binding property of an reassortant H5 HA/H1N1 influenza virus (Imai et al., 2012). Thus, identification of amino acid substitutions that increase viral thermostability would also be important risk assessment factors for emerging IAVs, such as those of subtypes H5 and 1-7 (Schrauwen et al., 2014). Moreover, in agreement with my observations. Watanabe et al. reported that HA thermostability was correlated with viral replication and glycan receptor binding of H5N1 viruses. However, further studies are needed to interpret the molecular mechanism of increased HA thermostability by mutations.

In conclusion, this study showed that the mutation Y161F in the RBS of the A(H1N1)pdm09 HA significantly increased viral yield in MDCK and Vero cells by promoting virus binding to both SA2,3GA and SA2,6GA without altering the original antigenicity. The results show that Y161F mutation in HA can be used in generating seed virus of high yield for influenza vaccine development and production.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, apparatus, apparatus elements, materials, procedures and techniques other than those specifically described herein can be applied to the practice of the invention as broadly disclosed herein without resort to undue experimentation. All art-known functional equivalents of methods, apparatus, apparatus elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims. All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present, application (for example, a reference that is partially inconsistent is incorporated by reference except for the partially inconsistent portion of the reference).

We claim:

1. The method of using Y161F mutation in hemagglutinin to generate seed virus of high yield for influenza vaccine development and production, comprising using site-directed mutagenesis to create mutation Y161F in hemagglutinin of influenza virus.

2. The method of claim 1, wherein the site-directed mutagenesis is performed using forward and reverse primers with SEQ ID NOs:1 and 2, respectively.

3. The method of claim 1, wherein the site-directed mutagenesis is performed using forward and reverse primers with SEQ ID NOs:3 and 4, respectively.

4. The method of claim 1, wherein the influenza virus is selected from the group consisting of: H1N1, H3N2, and H3N8 virus.

* * * * *

SEQUENCE LISTING

```
<160> NUMBER OF SEQ ID NOS: 52

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

ccacttaaac ttcaaattcc cagcattgaa cgtg                              34


<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

cacgttcaat gctgggaatt tgaagtttaa gtgg                              34
```

-continued

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
caaaatctgg aagctctttc cccacattga atgtgac 37

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gtcacattca atgtggggaa agagcttcca gattttg 37

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
tcatggccca atcatgactc gaac 24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tggggcattc accatccatc tact 24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
aacatatgta tctgcattct gata 24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
tagtgtccag taatagttca ttct 24

<210> SEQ ID NO 9
<211> LENGTH: 1701
<212> TYPE: DNA
<213> ORGANISM: Influenza A virus

<400> SEQUENCE: 9
atgaagacta tcattgcttt gagctacatt ctatgtctgg ttttcgctca aaaacttcct 60
ggaaatgaca atagcacggc aacgctgtgc cttgggcacc atgcagtacc aaacggaacg 120
atagtgaaaa caatcacgaa tgaccgaatt gaagttacta atgctactga actggttcag 180
aattcctcaa taggtgaaat atgcgacagt cctcatcaga tccttgatgg agaaaactgc 240
acactaatag atgctctatt gggagaccct cagtgtgatg gcttccaaaa taagaaatgg 300 gaccttttttg ttgaacgaag caaagcctac agcaactgtt acccttatga tgtgccggat 360
tatgcctccc ttaggtcact agttgcctca tccggcacac tggagtttaa caatgaaagc 420
ttcaattgga atggagtcac tcaaaacgga acaagttctg cttgcataag gagatctaat 480
aatagtttct ttagtagatt aaattggttg acccacttaa acttcaaata cccagcattg 540
aacgtgacta tgccaaacaa tgaacaattt gacaaattgt acatttgggg ggttcaccac 600
ccgggtacgg acaaggacca aatcttcctg tatgctcaac catcaggaag aatcacagta 660
tctaccaaaa gaagccaaca agctgtaatc ccgaatatcg gatctagacc cagaataagg 720
aatatcccta gcagaataag catctattgg acaatagtaa aaccgggaga catacttttg 780
attaacagca cagggaatct aattgctcct aggggttact tcaaaatacg aagtgggaaa 840
agctcaataa tgagatcaga tgcacccatt ggcaaatgca agtctgaatg catcactcca 900
aatggaagca ttcccaatga caaaccattc caaaatgtaa acaggatcac atacggggcc 960
tgtcccagat atgttaagca aagcactctg aaattggcaa caggaatgcg gaatgtacca 1020
gagaaacaaa ctagaggcat atttggcgca atagcgggtt tcatagaaaa tggttgggag 1080
ggaatggtgg atggttggta cggtttcagg catcaaaatt ctgagggaag aggacaagca 1140
gcagatctca aaagcactca agcagcaatc gatcaaatca atgggaagct gaatcgattg 1200
atcgggaaaa ccaacgagaa attccatcag attgaaaaag aattctcaga agtagaaggg 1260
agaattcagg accttgagaa atatgttgag gacactaaaa tagatctctg gtcatacaac 1320
gcggagcttc ttgttgccct ggagaaccaa catacaattg atctaactga ctcagaaatg 1380
aacaaactgt ttgaaaaaac aaagaagcaa ctgagggaaa atgctgagga tatgggcaat 1440
ggttgtttca aaatatacca caaatgtgac aatgcctgca taggatcaat cagaaatgga 1500
acttatgacc acgatgtata cagagatgaa gcattaaaca accggttcca gatcaaggga 1560
gttgagctga agtcagggta caaagattgg atcctatgga tttcctttgc catatcatgt 1620
tttttgcttt gtgttgcttt gttggggttc atcatgtggg cctgccaaaa gggcaacatt 1680
aggtgcaaca tttgcatttg a 1701

<210> SEQ ID NO 10
<211> LENGTH: 1701
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
atgaagacta tcattgcttt gagctacatt ctatgtctgg ttttcgctca aaaacttcct 60
ggaaatgaca atagcacggc aacgctgtgc cttgggcacc atgcagtacc aaacggaacg 120

-continued atagtgaaaa caatcacgaa tgaccgaatt gaagttacta atgctactga actggttcag 180
aattcctcaa taggtgaaat atgcgacagt cctcatcaga tccttgatgg agaaaactgc 240
acactaatag atgctctatt gggagaccct cagtgtgatg gcttccaaaa taagaaatgg 300
gacctttttg ttgaacgaag caaagcctac agcaactgtt acccttatga tgtgccggat 360
tatgcctccc ttaggtcact agttgcctca tccggcacac tggagtttaa caatgaaagc 420
ttcaattgga atggagtcac tcaaaacgga acaagttctg cttgcataag gagatctaat 480
aatagtttct ttagtagatt aaattggttg acccacttaa acttcaaatt cccagcattg 540
aacgtgacta tgccaaacaa tgaacaattt gacaaattgt acatttgggg ggttcaccac 600
ccgggtacgg acaaggacca aatcttcctg tatgctcaac catcaggaag aatcacagta 660
tctaccaaaa gaagccaaca agctgtaatc ccgaatatcg gatctagacc cagaataagg 720
aatatcccta gcagaataag catctattgg acaatagtaa aaccgggaga catacttttg 780
attaacagca cagggaatct aattgctcct aggggttact tcaaaatacg aagtgggaaa 840
agctcaataa tgagatcaga tgcacccatt ggcaaatgca agtctgaatg catcactcca 900
aatggaagca ttcccaatga caaaccattc caaaatgtaa acaggatcac atacggggcc 960
tgtcccagat atgttaagca aagcactctg aaattggcaa caggaatgcg gaatgtacca 1020
gagaaacaaa ctagaggcat atttggcgca atagcgggtt tcatagaaaa tggttgggag 1080
ggaatggtgg atggttggta cggtttcagg catcaaaatt ctgagggaag aggacaagca 1140
gcagatctca aaagcactca agcagcaatc gatcaaatca atgggaagct gaatcgattg 1200
atcgggaaaa ccaacgagaa attccatcag attgaaaaag aattctcaga agtagaaggg 1260
agaattcagg accttgagaa atatgttgag gacactaaaa tagatctctg gtcatacaac 1320
gcggagcttc ttgttgccct ggagaaccaa catacaattg atctaactga ctcagaaatg 1380
aacaaactgt ttgaaaaaac aaagaagcaa ctgagggaaa atgctgagga tatgggcaat 1440
ggttgtttca aaatatacca caaatgtgac aatgcctgca taggatcaat cagaaatgga 1500
acttatgacc acgatgtata cagagatgaa gcattaaaca accggttcca gatcaaggga 1560
gttgagctga agtcagggta caaagattgg atcctatgga tttcctttgc catatcatgt 1620
tttttgcttt gtgttgcttt gttggggttc atcatgtggg cctgccaaaa gggcaacatt 1680
aggtgcaaca tttgcatttg a 1701

<210> SEQ ID NO 11
<211> LENGTH: 1698
<212> TYPE: DNA
<213> ORGANISM: Influenza A virus

<400> SEQUENCE: 11
atgaagacaa ccattatttt aatactactg acccattggg cctacagtca aaacccaatc 60
agtggcaata acacagccac actgtgtctg ggacaccatg cagtagcaaa tggaacattg 120
gtaaaaacaa tgagtgatga tcaaattgag gtgacaaatg ctacagaatt agttcagagc 180
atttcaatgg ggaaaatatg caacaaatca tatagaattc tagatggaag aaattgcaca 240
ttaatagatg caatgctagg agacccccac tgtgacgccc ttcagtatga gagttgggac 300
ctctttatag aaagaagcag cgctttcagc aattgctacc catatgacat ccctgactat 360
gcatcgctcc gatccattgt agcatcctca ggaacagttg aattcacagc agagggattc 420
acatggacag gtgtaactca aaacggaaga agtggagcct gcaaaagggg atcagccgat 480
agtttcttta gccgactgaa ttggctaaca aaatctggaa gctcttaccc cacattgaat 540
gtgacaatgc ctaacaataa aaatttcgac aagctataca tctgggggat tcatcacccg 600
agctcaaatc aagagcagac aaaattgtac atccaagaat caggacgagt aacagtctca 660
acaaaaagaa gtcaacaaac aataatccct aacatcgaat ctagaccgtt ggtcagaggt 720
caatcaggca ggataagcat atactggacc attgtaaaac ctggagatat cctaatgata 780
aacagtaatg gcaacttagt tgcaccgcgg ggatatttta aattgaacac agggaaaagc 840
tctgtaatga gatccgatgt acccatagac atttgtgtgt ctgaatgtat tacaccaaat 900
ggaagcatct ccaacgacaa gccattccaa aatgtgaaca aagttacata tggaaaatgc 960
cccaagtata tcaggcaaaa cactttaaag ctggccactg ggatgaggaa tgtaccagaa 1020
aagcaaacca gaggaatctt tggagcaata gcgggattca tcgaaaacgg ctgggaagga 1080
atggttgatg ggtggtatgg gttccgatat caaaactctg aaggaacagg gcaagctgca 1140
gatctaaaga gcactcaagc agccattgac cagattaatg gaaagttaaa cagagtgatt 1200
gaaagaacca atgagaaatt ccatcaaata gagaaggaat tctcagaagt agaaggaaga 1260
attcaggact tggagaaata tgtagaagac accaaaatag acctatggtc ctacaatgca 1320
gaattgctgg tggctctaga aaatcaacat acaattgact taacagatgc agaaatgaat 1380
aaattatttg agaagactag acgccagtta agagaaaacg cagaagacat gggaggtgga 1440
tgtttcaaga tttaccacaa atgtgataat gcatgcattg aatcaataag aactgggaca 1500
tatgaccatt acatatacag agatgaagca ttaaacaacc gatttcagat caaaggtgta 1560
gagttgaaat caggctacaa agattggata ctgtggattt cattcgccat atcatgcttc 1620
ttaatttgcg ttgttctatt gggtttcatt atgtgggctt gccaaaaagg caacatcaga 1680
tgcaacattt gcatttga 1698

<210> SEQ ID NO 12
<211> LENGTH: 1698
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
atgaagacaa ccattatttt aatactactg acccattggg cctacagtca aaacccaatc 60
agtggcaata acacagccac actgtgtctg ggacaccatg cagtagcaaa tggaacattg 120
gtaaaaacaa tgagtgatga tcaaattgag gtgacaaatg ctacagaatt agttcagagc 180
atttcaatgg ggaaaatatg caacaaatca tatagaattc tagatggaag aaattgcaca 240
ttaatagatg caatgctagg agacccccac tgtgacgccc ttcagtatga gagttgggac 300
ctctttatag aaagaagcag cgctttcagc aattgctacc catatgacat ccctgactat 360
gcatcgctcc gatccattgt agcatcctca ggaacagttg aattcacagc agagggattc 420
acatggacag gtgtaactca aaacggaaga agtggagcct gcaaaagggg atcagccgat 480
agtttcttta gccgactgaa ttggctaaca aaatctggaa gctctttccc cacattgaat 540
gtgacaatgc ctaacaataa aaatttcgac aagctataca tctgggggat tcatcacccg 600
agctcaaatc aagagcagac aaaattgtac atccaagaat caggacgagt aacagtctca 660
acaaaaagaa gtcaacaaac aataatccct aacatcgaat ctagaccgtt ggtcagaggt 720
caatcaggca ggataagcat atactggacc attgtaaaac ctggagatat cctaatgata 780

-continued

```
aacagtaatg gcaacttagt tgcaccgcgg ggatatttta aattgaacac agggaaaagc     840
tctgtaatga gatccgatgt acccatagac atttgtgtgt ctgaatgtat tacaccaaat     900
ggaagcatct ccaacgacaa gccattccaa aatgtgaaca aagttacata tggaaaatgc     960
cccaagtata tcaggcaaaa cactttaaag ctggccactg ggatgaggaa tgtaccagaa    1020
aagcaaacca gaggaatctt tggagcaata gcgggattca tcgaaaacgg ctgggaagga    1080
atggttgatg ggtggtatgg gttccgatat caaaactctg aaggaacagg gcaagctgca    1140
gatctaaaga gcactcaagc agccattgac cagattaatg gaaagttaaa cagagtgatt    1200
gaaagaacca atgagaaatt ccatcaaata gagaaggaat tctcagaagt agaaggaaga    1260
attcaggact tggagaaata tgtagaagac accaaaatag acctatggtc ctacaatgca    1320
gaattgctgg tggctctaga aaatcaacat acaattgact taacagatgc agaaatgaat    1380
aaattatttg agaagactag acgccagtta agagaaaacg cagaagacat gggaggtgga    1440
tgtttcaaga tttaccacaa atgtgataat gcatgcattg aatcaataag aactgggaca    1500
tatgaccatt acatatacag agatgaagca ttaaacaacc gatttcagat caaaggtgta    1560
gagttgaaat caggctacaa agattggata ctgtggattt cattcgccat atcatgcttc    1620
ttaatttgcg ttgttctatt gggtttcatt atgtgggctt gccaaaaagg caacatcaga    1680
tgcaacattt gcatttga                                                  1698
```

```
<210> SEQ ID NO 13
<211> LENGTH: 1701
<212> TYPE: DNA
<213> ORGANISM: Influenza A virus

<400> SEQUENCE: 13
```

```
atgaaggcaa tactagtagt tctgctatat acatttgcaa ccgcaaatgc agacacatta      60
tgtataggtt atcatgcgaa caattcaaca gacactgtag acacagtact agaaaagaat     120
gtaacagtaa cacactctgt taaccttcta gaagacaagc ataacgggaa actatgcaaa     180
ctaagagggg tagccccatt gcatttgggt aaatgtaaca ttgctggctg gatcctggga     240
aatccagagt gtgaatcact ctccacagca agctcatggt cctacattgt ggaaacacct     300
agttcagaca atggaacgtg ttacccagga gatttcatcg attatgagga gctaagagag     360
caattgagct cggtgtcatc atttgaaagg tttgagatat tccccaagac aagttcatgg     420
cccaatcatg actcgaacaa aggtgtaacg gcagcatgtc ctcatgctgg agcaaaaagc     480
ttctacaaaa atttaatatg gctagttaaa aaaggaaatt catacccaaa gctcagcaaa     540
tcctacatta atgataaagg gaaagaagtc ctcgtgctat ggggcattca ccatccatct     600
actagtgctg accaacaaag tatctatcag aatgcagata catatgtttt tgtggggtca     660
tcaagataca gcaagaagtt caagccggaa atagcaataa gacccaaagt gagggatcaa     720
gaagggagaa tgaactatta ctggacacta gtagagccgg gagacaaaat aacattcgaa     780
gcaactggaa atctagtggt accgagatat gcattcgcaa tggaaagaaa tgctggatct     840
ggtattatca tttcagatac accagtccac gattgcaata caacttgtca aacacccaag     900
ggtgctataa acaccagcct cccatttcag aatatacatc cgatcacaat tggaaaatgt     960
ccaaaatatg taaaaagcac aaaattgaga ctggccacag gattgaggaa tatcccgtct    1020
attcaatcta gaggcctatt tggggccatt gccggtttca ttgaaggggg gtggacaggg    1080
atggtagatg gatggtacgg ttatcaccat caaaatgagc aggggtcagg atatgcagcc    1140
gacctgaaga gcacacagaa tgccattgac gagattacta acaaagtaaa ttctgttatt    1200
```

gaaaagatga atacacagtt cacagcagta ggtaaagagt tcaaccacct ggaaaaaaga 1260
atagagaatt taaataaaaa agttgatgat ggtttcctgg acatttggac ttacaatgcc 1320
gaactgttgg ttctattgga aaatgaaaga actttggact accacgattc aaatgtgaag 1380
aacttatatg aaaaggtaag aagccagcta aaaaacaatg ccaaggaaat tggaaacggc 1440
tgctttgaat tttaccacaa atgcgataac acgtgcatgg aaagtgtcaa aaatgggact 1500
tatgactacc caaaatactc agaggaagca aaattaaaca gagaagaaat agatggggta 1560
aagctggaat caacaaggat ttaccagatt ttggcgatct attcaactgt cgccagttca 1620
ttggtactgg tagtctccct gggggcaatc agtttctgga tgtgctctaa tgggtctcta 1680
cagtgtagaa tatgtattta a 1701

<210> SEQ ID NO 14
<211> LENGTH: 1701
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14
atgaaggcaa tactagtagt tctgctatat acatttgcaa ccgcaaatgc agacacatta 60
tgtataggtt atcatgcgaa caattcaaca gacactgtag acacagtact agaaaagaat 120
gtaacagtaa cacactctgt taaccttcta gaagacaagc ataacgggaa actatgcaaa 180
ctaagagggg tagccccatt gcatttgggt aaatgtaaca ttgctggctg gatcctggga 240
aatccagagt gtgaatcact ctccacagca agctcatggt cctacattgt ggaaacacct 300
agttcagaca atggaacgtg ttacccagga gatttcatcg attatgagga gctaagagag 360
caattgagct cggtgtcatc atttgaaagg tttgagatat tccccaagac aagttcatgg 420
cccaatcatg actcgaacaa aggtgtaacg gcagcatgtc ctcatgctgg agcaaaaagc 480
ttctacaaaa atttaatatg gctagttaaa aaaggaaatt cattcccaaa gctcagcaaa 540
tcctacatta atgataaagg gaaagaagtc ctcgtgctat ggggcattca ccatccatct 600
actagtgctg accaacaaag tatctatcag aatgcagata catatgtttt tgtggggtca 660
tcaagataca gcaagaagtt caagccggaa atagcaataa gacccaaagt gagggatcaa 720
gaagggagaa tgaactatta ctggacacta gtagagccgg gagacaaaat aacattcgaa 780
gcaactggaa atctagtggt accgagatat gcattcgcaa tggaaagaaa tgctggatct 840
ggtattatca tttcagatac accagtccac gattgcaata caacttgtca aacacccaag 900
ggtgctataa acaccagcct cccatttcag aatatacatc cgatcacaat tggaaaatgt 960
ccaaaatatg taaaaagcac aaaattgaga ctggccacag gattgaggaa tatcccgtct 1020
attcaatcta gaggcctatt tggggccatt gccggtttca ttgaaggggg gtggacaggg 1080
atggtagatg gatggtacgg ttatcaccat caaaatgagc aggggtcagg atatgcagcc 1140
gacctgaaga gcacacagaa tgccattgac gagattacta acaaagtaaa ttctgttatt 1200
gaaaagatga atacacagtt cacagcagta ggtaaagagt tcaaccacct ggaaaaaaga 1260
atagagaatt taaataaaaa agttgatgat ggtttcctgg acatttggac ttacaatgcc 1320
gaactgttgg ttctattgga aaatgaaaga actttggact accacgattc aaatgtgaag 1380
aacttatatg aaaaggtaag aagccagcta aaaaacaatg ccaaggaaat tggaaacggc 1440
tgctttgaat tttaccacaa atgcgataac acgtgcatgg aaagtgtcaa aaatgggact 1500

```
tatgactacc caaaatactc agaggaagca aaattaaaca gagaagaaat agatggggta   1560

aagctggaat caacaaggat ttaccagatt ttggcgatct attcaactgt cgccagttca   1620

ttggtactgg tagtctccct gggggcaatc agtttctgga tgtgctctaa tgggtctcta   1680

cagtgtagaa tatgtattta a                                             1701
```

<210> SEQ ID NO 15
<211> LENGTH: 1701
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
atgaaggcaa tactagtagt tctgctatat acatttgcaa ccgcaaatgc agacacatta     60

tgtataggtt atcatgcgaa caattcaaca gacactgtag acacagtact agaaaagaat    120

gtaacagtaa cacactctgt taaccttcta gaagacaagc ataacgggaa actatgcaaa    180

ctaagagggg tagccccatt gcatttgggt aaatgtaaca ttgctggctg gatcctggga    240

aatccagagt gtgaatcact ctccacagca agctcatggt cctacattgt ggaaacacct    300

agttcagaca atggaacgtg ttacccagga gatttcatcg attatgagga gctaagagag    360

caattgagct cggtgtcatc atttgaaagg tttgagatat tccccaagac aagttcatgg    420

cccaatcatg actcgaacaa aggtgtaacg gcagcatgta ctcatgctgg agcaaaaagc    480

ttctacaaaa atttaatatg gctagttaaa aaaggaaatt catacccaaa gctcagcaaa    540

tcctacatta atgataaagg gaaagaagtc ctcgtgctat ggggcattca ccatccatct    600

actagtgctg accaacaaag tatctatcag aatgcagata catatgtttt tgtggggtca    660

tcaagataca gcaagaagtt caagccggaa atagcaataa gacccaaagt gagggatcaa    720

gaagggagaa tgaactatta ctggacacta gtagagccgg gagacaaaat aacattcgaa    780

gcaactggaa atctagtggt accgagatat gcattcgcaa tggaaagaaa tgctggatct    840

ggtattatca tttcagatac accagtccac gattgcaata caacttgtca aacacccaag    900

ggtgctataa acaccagcct cccatttcag aatatacatc cgatcacaat tggaaaatgt    960

ccaaaatatg taaaaagcac aaaattgaga ctggccacag gattgaggaa tatcccgtct   1020

attcaatcta gaggcctatt tggggccatt gccggtttca ttgaaggggg gtggacaggg   1080

atggtagatg gatggtacgg ttatcaccat caaaatgagc aggggtcagg atatgcagcc   1140

gacctgaaga gcacacagaa tgccattgac gagattacta acaaagtaaa ttctgttatt   1200

gaaaagatga atacacagtt cacagcagta ggtaaagagt tcaaccacct ggaaaaaaga   1260

atagagaatt taaataaaaa agttgatgat ggtttcctgg acatttggac ttacaatgcc   1320

gaactgttgg ttctattgga aaatgaaaga actttggact accacgattc aaatgtgaag   1380

aacttatatg aaaaggtaag aagccagcta aaaaacaatg ccaaggaaat tggaaacggc   1440

tgctttgaat tttaccacaa atgcgataac acgtgcatgg aaagtgtcaa aaatgggact   1500

tatgactacc caaaatactc agaggaagca aaattaaaca gagaagaaat agatggggta   1560

aagctggaat caacaaggat ttaccagatt ttggcgatct attcaactgt cgccagttca   1620

ttggtactgg tagtctccct gggggcaatc agtttctgga tgtgctctaa tgggtctcta   1680

cagtgtagaa tatgtattta a                                             1701
```

<210> SEQ ID NO 16
<211> LENGTH: 1701
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 16

```
atgaaggcaa tactagtagt tctgctatat acatttgcaa ccgcaaatgc agacacatta     60

tgtataggtt atcatgcgaa caattcaaca gacactgtag acacagtact agaaaagaat    120

gtaacagtaa cacactctgt taaccttcta gaagacaagc ataacgggaa actatgcaaa    180

ctaagagggg tagccccatt gcatttgggt aaatgtaaca ttgctggctg gatcctggga    240

aatccagagt gtgaatcact ctccacagca agctcatggt cctacattgt ggaaacacct    300

agttcagaca atggaacgtg ttacccagga gatttcatcg attatgagga gctaagagag    360

caattgagct cggtgtcatc atttgaaagg tttgagatat tccccaagac aagttcatgg    420

cccaatcatg actcgaacaa aggtgtaacg gcagcatgtc ctcatgctgg agcaaaaagc    480

ttctacaaaa atttaatatg gctagttaaa aaaggaaatt catacccaaa gctcagcaaa    540

tcctacatta atgataaagg gaaagaagtc ctcgtgctat ggggcattca ccatccatct    600

actattgctg accaacaaag tatctatcag aatgcagata catatgtttt tgtggggtca    660

tcaagataca gcaagaagtt caagccggaa atagcaataa gacccaaagt gagggatcaa    720

gaagggagaa tgaactatta ctggacacta gtagagccgg gagacaaaat aacattcgaa    780

gcaactggaa atctagtggt accgagatat gcattcgcaa tggaaagaaa tgctggatct    840

ggtattatca tttcagatac accagtccac gattgcaata caacttgtca aacacccaag    900

ggtgctataa acaccagcct cccatttcag aatatacatc cgatcacaat tggaaaatgt    960

ccaaaatatg taaaaagcac aaaattgaga ctggccacag gattgaggaa tatcccgtct   1020

attcaatcta gaggcctatt tggggccatt gccggtttca ttgaaggggg gtggacaggg   1080

atggtagatg gatggtacgg ttatcaccat caaaatgagc aggggtcagg atatgcagcc   1140

gacctgaaga gcacacagaa tgccattgac gagattacta acaaagtaaa ttctgttatt   1200

gaaaagatga atacacagtt cacagcagta ggtaaagagt tcaaccacct ggaaaaaaga   1260

atagagaatt taaataaaaa agttgatgat ggtttcctgg acatttggac ttacaatgcc   1320

gaactgttgg ttctattgga aaatgaaaga actttggact accacgattc aaatgtgaag   1380

aacttatatg aaaaggtaag aagccagcta aaaaacaatg ccaaggaaat tggaaacggc   1440

tgctttgaat tttaccacaa atgcgataac acgtgcatgg aaagtgtcaa aaatgggact   1500

tatgactacc caaaatactc agaggaagca aaattaaaca gagaagaaat agatggggta   1560

aagctggaat caacaaggat ttaccagatt ttggcgatct attcaactgt cgccagttca   1620

ttggtactgg tagtctccct gggggcaatc agtttctgga tgtgctctaa tgggtctcta   1680

cagtgtagaa tatgtattta a                                             1701
```

<210> SEQ ID NO 17
<211> LENGTH: 1701
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17

```
atgaaggcaa tactagtagt tctgctatat acatttgcaa ccgcaaatgc agacacatta      60

tgtataggtt atcatgcgaa caattcaaca gacactgtag acacagtact agaaaagaat     120

gtaacagtaa cacactctgt taaccttcta gaagacaagc ataacgggaa actatgcaaa     180

ctaagagggg tagccccatt gcatttgggt aaatgtaaca ttgctggctg gatcctggga     240

aatccagagt gtgaatcact ctccacagca agctcatggt cctacattgt ggaaacacct     300

agttcagaca atggaacgtg ttacccagga gatttcatcg attatgagga gctaagagag     360

caattgagct cggtgtcatc atttgaaagg tttgagatat tccccaagac aagttcatgg     420

cccaatcatg actcgaacaa aggtgtaacg gcagcatgtc ctcatgctgg agcaaaaagc     480

ttctacaaaa atttaatatg gctagttaaa aaaggaaata catacccaaa gctcagcaaa     540

tcctacatta atgataaagg gaaagaagtc ctcgtgctat ggggcattca ccatccatct     600

actagtgctg accaacaaag tatctatcag aatgcagata catatgtttt tgtggggtca     660

tcaagataca gcaagaagtt caagccggaa atagcaataa gacccaaagt gagggatcaa     720

gaagggagaa tgaactatta ctggacacta gtagagccgg gagacaaaat aacattcgaa     780

gcaactggaa atctagtggt accgagatat gcattcgcaa tggaaagaaa tgctggatct     840

ggtattatca tttcagatac accagtccac gattgcaata caacttgtca aacacccaag     900

ggtgctataa acaccagcct cccatttcag aatatacatc cgatcacaat tggaaaatgt     960

ccaaaatatg taaaaagcac aaaattgaga ctggccacag gattgaggaa tatcccgtct    1020

attcaatcta gaggcctatt tggggccatt gccggtttca ttgaaggggg gtggacaggg    1080

atggtagatg gatggtacgg ttatcaccat caaaatgagc aggggtcagg atatgcagcc    1140

gacctgaaga gcacacagaa tgccattgac gagattacta acaaagtaaa ttctgttatt    1200

gaaaagatga atacacagtt cacagcagta ggtaaagagt tcaaccacct ggaaaaaaga    1260

atagagaatt taaataaaaa agttgatgat ggtttcctgg acatttggac ttacaatgcc    1320

gaactgttgg ttctattgga aaatgaaaga actttggact accacgattc aaatgtgaag    1380

aacttatatg aaaaggtaag aagccagcta aaaaacaatg ccaaggaaat tggaaacggc    1440

tgctttgaat tttaccacaa atgcgataac acgtgcatgg aaagtgtcaa aaatgggact    1500

tatgactacc caaaatactc agaggaagca aaattaaaca gagaagaaat agatggggta    1560

aagctggaat caacaaggat ttaccagatt ttggcgatct attcaactgt cgccagttca    1620

ttggtactgg tagtctccct gggggcaatc agtttctgga tgtgctctaa tgggtctcta    1680

cagtgtagaa tatgtattta a                                              1701
```

<210> SEQ ID NO 18
<211> LENGTH: 1701
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atgaaggcaa tactagtagt tctgctatat acatttgcaa ccgcaaatgc agacacatta      60

tgtataggtt atcatgcgaa caattcaaca gacactgtag acacagtact agaaaagaat     120

gtaacagtaa cacactctgt taaccttcta gaagacaagc ataacgggaa actatgcaaa     180

ctaagagggg tagccccatt gcatttgggt aaatgtaaca ttgctggctg gatcctggga     240

aatccagagt gtgaatcact ctccacagca agctcatggt cctacattgt ggaaacacct     300
```

```
agttcagaca atggaacgtg ttacccagga gatttcatcg attatgagga gctaagagag    360

caattgagct cggtgtcatc atttgaaagg tttgagatat tccccaagac aagttcatgg    420

cccaatcatg actcgaacaa aggtgtaacg gcagcatgtc ctcatgctgg agcaaaaagc    480

ttctacaaaa atttaatatg gctagttaaa aaaggaaatt catacccaaa gctcagcaaa    540

tcctacatta atgataaagg gaaagaagtc ctcgtgctat ggggcattca ccatccatct    600

actagtgctg accaacaaag tatctatcag aatgcagata cacatgtttt tgtggggtca    660

tcaagataca gcaagaagtt caagccggaa atagcaataa gacccaaagt gagggatcaa    720

gaagggagaa tgaactatta ctggacacta gtagagccgg gagacaaaat aacattcgaa    780

gcaactggaa atctagtggt accgagatat gcattcgcaa tggaaagaaa tgctggatct    840

ggtattatca tttcagatac accagtccac gattgcaata caacttgtca aacacccaag    900

ggtgctataa acaccagcct cccatttcag aatatacatc cgatcacaat tggaaaatgt    960

ccaaaatatg taaaaagcac aaaattgaga ctggccacag gattgaggaa tatcccgtct   1020

attcaatcta gaggcctatt tggggccatt gccggtttca ttgaaggggg gtggacaggg   1080

atggtagatg gatggtacgg ttatcaccat caaaatgagc aggggtcagg atatgcagcc   1140

gacctgaaga gcacacagaa tgccattgac gagattacta acaaagtaaa ttctgttatt   1200

gaaaagatga atacacagtt cacagcagta ggtaaagagt tcaaccacct ggaaaaaaga   1260

atagagaatt taaataaaaa agttgatgat ggtttcctgg acatttggac ttacaatgcc   1320

gaactgttgg ttctattgga aaatgaaaga actttggact accacgattc aaatgtgaag   1380

aacttatatg aaaaggtaag aagccagcta aaaaacaatg ccaaggaaat tggaaacggc   1440

tgctttgaat tttaccacaa atgcgataac acgtgcatgg aaagtgtcaa aaatgggact   1500

tatgactacc caaaatactc agaggaagca aaattaaaca gagaagaaat agatggggta   1560

aagctggaat caacaaggat ttaccagatt ttggcgatct attcaactgt cgccagttca   1620

ttggtactgg tagtctccct gggggcaatc agtttctgga tgtgctctaa tgggtctcta   1680

cagtgtagaa tatgtattta a                                              1701
```

<210> SEQ ID NO 19
<211> LENGTH: 1701
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
atgaaggcaa tactagtagt tctgctatat acatttgcaa ccgcaaatgc agacacatta     60

tgtataggtt atcatgcgaa caattcaaca gacactgtag acacagtact agaaaagaat    120

gtaacagtaa cacactctgt taaccttcta gaagacaagc ataacgggaa actatgcaaa    180

ctaagagggg tagccccatt gcatttgggt aaatgtaaca ttgctggctg gatcctggga    240

aatccagagt gtgaatcact ctccacagca agctcatggt cctacattgt ggaaacacct    300

agttcagaca atggaacgtg ttacccagga gatttcatcg attatgagga gctaagagag    360

caattgagct cggtgtcatc atttgaaagg tttgagatat tccccaagac aagttcatgg    420

cccaatcatg aatcgaacaa aggtgtaacg gcagcatgtc ctcatgctgg agcaaaaagc    480

ttctacaaaa atttaatatg gctagttaaa aaaggaaatt catacccaaa gctcagcaaa    540

tcctacatta atgataaagg gaaagaagtc ctcgtgctat ggggcattca ccatccatct    600
```

-continued

```
actagtgctg accaacaaag tatctatcag aatgcagata catatgtttt tgtggggtca    660

tcaagataca gcaagaagtt caagccggaa atagcaataa gacccaaagt gagggatcaa    720

gaagggagaa tgaactatta ctggacacta gtagagccgg gagacaaaat aacattcgaa    780

gcaactggaa atctagtggt accgagatat gcattcgcaa tggaaagaaa tgctggatct    840

ggtattatca tttcagatac accagtccac gattgcaata caacttgtca aacacccaag    900

ggtgctataa acaccagcct cccatttcag aatatacatc cgatcacaat tggaaaatgt    960

ccaaaatatg taaaaagcac aaaattgaga ctggccacag gattgaggaa tatcccgtct   1020

attcaatcta gaggcctatt tggggccatt gccggtttca ttgaaggggg gtggacaggg   1080

atggtagatg gatggtacgg ttatcaccat caaaatgagc aggggtcagg atatgcagcc   1140

gacctgaaga gcacacagaa tgccattgac gagattacta acaaagtaaa ttctgttatt   1200

gaaaagatga atacacagtt cacagcagta ggtaaagagt tcaaccacct ggaaaaaaga   1260

atagagaatt taaataaaaa agttgatgat ggtttcctgg acatttggac ttacaatgcc   1320

gaactgttgg ttctattgga aaatgaaaga actttggact accacgattc aaatgtgaag   1380

aacttatatg aaaaggtaag aagccagcta aaaaacaatg ccaaggaaat tggaaacggc   1440

tgctttgaat tttaccacaa atgcgataac acgtgcatgg aaagtgtcaa aaatgggact   1500

tatgactacc caaaatactc agaggaagca aaattaaaca gagaagaaat agatggggta   1560

aagctggaat caacaaggat ttaccagatt ttggcgatct attcaactgt cgccagttca   1620

ttggtactgg tagtctccct gggggcaatc agtttctgga tgtgctctaa tgggtctcta   1680

cagtgtagaa tatgtattta a                                             1701
```

<210> SEQ ID NO 20
<211> LENGTH: 1701
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
atgaaggcaa tactagtagt tctgctatat acatttgcaa ccgcaaatgc agacacatta     60

tgtataggtt atcatgcgaa caattcaaca gacactgtag acacagtact agaaaagaat    120

gtaacagtaa cacactctgt taaccttcta gaagacaagc ataacgggaa actatgcaaa    180

ctaagagggg tagccccatt gcatttgggt aaatgtaaca ttgctggctg gatcctggga    240

aatccagagt gtgaatcact ctccacagca agctcatggt cctacattgt ggaaacacct    300

agttcagaca atggaacgtg ttacccagga gatttcatcg attatgagga gctaagagag    360

caattgagct cggtgtcatc atttgaaagg tttgagatat tccccaagac aagttcatgg    420

cccaatcatg actcgaacaa aggtgtaacg gcagcatgtc ctcatgctgg agcaaaaagc    480

ttctacaaaa atttaatatg gctagttaaa aaaggaaatt catacccaaa gctcagcaaa    540

tcctacatta atgataaagg ggaagaagtc ctcgtgctat ggggcattca ccatccatct    600

actagtgctg accaacaaag tatctatcag aatgcagata catatgtttt tgtggggtca    660

tcaagataca gcaagaagtt caagccggaa atagcaataa gacccaaagt gagggatcaa    720

gaagggagaa tgaactatta ctggacacta gtagagccgg gagacaaaat aacattcgaa    780

gcaactggaa atctagtggt accgagatat gcattcgcaa tggaaagaaa tgctggatct    840

ggtattatca tttcagatac accagtccac gattgcaata caacttgtca aacacccaag    900
```

ggtgctataa acaccagcct cccatttcag aatatacatc cgatcacaat tggaaaatgt 960
ccaaaatatg taaaaagcac aaaattgaga ctggccacag gattgaggaa tatcccgtct 1020
attcaatcta gaggcctatt tggggccatt gccggtttca ttgaaggggg gtggacaggg 1080
atggtagatg gatggtacgg ttatcaccat caaaatgagc aggggtcagg atatgcagcc 1140
gacctgaaga gcacacagaa tgccattgac gagattacta acaaagtaaa ttctgttatt 1200
gaaaagatga atacacagtt cacagcagta ggtaaagagt tcaaccacct ggaaaaaaga 1260
atagagaatt taaataaaaa agttgatgat ggtttcctgg acatttggac ttacaatgcc 1320
gaactgttgg ttctattgga aaatgaaaga actttggact accacgattc aaatgtgaag 1380
aacttatatg aaaaggtaag aagccagcta aaaaacaatg ccaaggaaat tggaaacggc 1440
tgctttgaat tttaccacaa atgcgataac acgtgcatgg aaagtgtcaa aaatgggact 1500
tatgactacc caaaatactc agaggaagca aaattaaaca gagaagaaat agatggggta 1560
aagctggaat caacaaggat ttaccagatt ttggcgatct attcaactgt cgccagttca 1620
ttggtactgg tagtctccct gggggcaatc agtttctgga tgtgctctaa tgggtctcta 1680
cagtgtagaa tatgtattta a 1701

<210> SEQ ID NO 21
<211> LENGTH: 1701
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21
atgaaggcaa tactagtagt tctgctatat acatttgcaa ccgcaaatgc agacacatta 60
tgtataggtt atcatgcgaa caattcaaca gacactgtag acacagtact agaaaagaat 120
gtaacagtaa cacactctgt taaccttcta gaagacaagc ataacgggaa actatgcaaa 180
ctaagagggg tagccccatt gcatttgggt aaatgtaaca ttgctggctg gatcctggga 240
aatccagagt gtgaatcact ctccacagca agctcatggt cctacattgt ggaaacacct 300
agttcagaca atggaacgtg ttacccagga gatttcatcg attatgagga gctaagagag 360
caattgagct cggtgtcatc atttgaaagg tttgagatat tccccaagac aagttcatgg 420
cccaatcatg actcgaacaa aggtgtaacg gcagcatgtc ctcatgctgg agcaaaaagc 480
ttctacaaaa atttaatatg gtttgttcaa aaaggaaatt catacccaaa gctcagcaaa 540
tcctacatta atgataaagg gaaagaagtc ctcgtgctat ggggcattca ccatccatct 600
actagtgctg accaacaaag tatctatcag aatgcagata catatgtttt tgtggggtca 660
tcaagataca gcaagaagtt caagccggaa atagcaataa gacccaaagt gagggatcaa 720
gaagggagaa tgaactatta ctggacacta gtagagccgg gagacaaaat aacattcgaa 780
gcaactggaa atctagtggt accgagatat gcattcgcaa tggaaagaaa tgctggatct 840
ggtattatca tttcagatac accagtccac gattgcaata caacttgtca aacacccaag 900
ggtgctataa acaccagcct cccatttcag aatatacatc cgatcacaat tggaaaatgt 960
ccaaaatatg taaaaagcac aaaattgaga ctggccacag gattgaggaa tatcccgtct 1020
attcaatcta gaggcctatt tggggccatt gccggtttca ttgaaggggg gtggacaggg 1080
atggtagatg gatggtacgg ttatcaccat caaaatgagc aggggtcagg atatgcagcc 1140
gacctgaaga gcacacagaa tgccattgac gagattacta acaaagtaaa ttctgttatt 1200

```
gaaaagatga atacacagtt cacagcagta ggtaaagagt tcaaccacct ggaaaaaaga   1260

atagagaatt taaataaaaa agttgatgat ggtttcctgg acatttggac ttacaatgcc   1320

gaactgttgg ttctattgga aaatgaaaga actttggact accacgattc aaatgtgaag   1380

aacttatatg aaaaggtaag aagccagcta aaaaacaatg ccaaggaaat tggaaacggc   1440

tgctttgaat tttaccacaa atgcgataac acgtgcatgg aaagtgtcaa aaatgggact   1500

tatgactacc caaaatactc agaggaagca aaattaaaca gagaagaaat agatggggta   1560

aagctggaat caacaaggat ttaccagatt ttggcgatct attcaactgt cgccagttca   1620

ttggtactgg tagtctccct gggggcaatc agtttctgga tgtgctctaa tgggtctcta   1680

cagtgtagaa tatgtattta a                                               1701


<210> SEQ ID NO 22
<211> LENGTH: 566
<212> TYPE: PRT
<213> ORGANISM: Influenza A virus

<400> SEQUENCE: 22

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Asn
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Pro Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285
```

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 23
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys

```
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Asn
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Phe Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Pro Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495
```

```
Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565


<210> SEQ ID NO 24
<211> LENGTH: 565
<212> TYPE: PRT
<213> ORGANISM: Influenza A virus

<400> SEQUENCE: 24

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
            20                  25                  30

His Ala Val Ala Asn Gly Thr Leu Val Lys Thr Met Ser Asp Asp Gln
        35                  40                  45

Ile Glu Val Thr Asn Ala Thr Glu Leu Val Gln Ser Ile Ser Met Gly
    50                  55                  60

Lys Ile Cys Asn Lys Ser Tyr Arg Ile Leu Asp Gly Arg Asn Cys Thr
65                  70                  75                  80

Leu Ile Asp Ala Met Leu Gly Asp Pro His Cys Asp Ala Leu Gln Tyr
                85                  90                  95

Glu Ser Trp Asp Leu Phe Ile Glu Arg Ser Ser Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Val Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
    210                 215                 220

Gln Gln Thr Ile Ile Pro Asn Ile Glu Ser Arg Pro Leu Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Asn Thr Gly Lys Ser Ser Val Met Arg Ser Asp Val Pro
        275                 280                 285

Ile Asp Ile Cys Val Ser Glu Cys Ile Thr Pro Asn Gly Ser Ile Ser
```

```
    290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Thr Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
    450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Glu Ser Ile
                485                 490                 495

Arg Thr Gly Thr Tyr Asp His Tyr Ile Tyr Arg Asp Glu Ala Leu Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565


<210> SEQ ID NO 25
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
            20                  25                  30

His Ala Val Ala Asn Gly Thr Leu Val Lys Thr Met Ser Asp Asp Gln
        35                  40                  45

Ile Glu Val Thr Asn Ala Thr Glu Leu Val Gln Ser Ile Ser Met Gly
    50                  55                  60

Lys Ile Cys Asn Lys Ser Tyr Arg Ile Leu Asp Gly Arg Asn Cys Thr
65                  70                  75                  80
```

```
Leu Ile Asp Ala Met Leu Gly Asp Pro His Cys Asp Ala Leu Gln Tyr
                85                  90                  95

Glu Ser Trp Asp Leu Phe Ile Glu Arg Ser Ser Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Val Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Phe
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
    210                 215                 220

Gln Gln Thr Ile Ile Pro Asn Ile Glu Ser Arg Pro Leu Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Asn Thr Gly Lys Ser Ser Val Met Arg Ser Asp Val Pro
        275                 280                 285

Ile Asp Ile Cys Val Ser Glu Cys Ile Thr Pro Asn Gly Ser Ile Ser
    290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Thr Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
    450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Glu Ser Ile
                485                 490                 495

Arg Thr Gly Thr Tyr Asp His Tyr Ile Tyr Arg Asp Glu Ala Leu Asn
```

```
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565


<210> SEQ ID NO 26
<211> LENGTH: 566
<212> TYPE: PRT
<213> ORGANISM: Influenza A virus

<400> SEQUENCE: 26

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Thr Ile
        195                 200                 205

Tyr Gln Asn Ser Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300
```

-continued

```
Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 27
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95
```

```
Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Phe Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Thr Ile
        195                 200                 205

Tyr Gln Asn Ser Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510
```

```
Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 28
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Thr His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Thr Ile
        195                 200                 205

Tyr Gln Asn Ser Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300
```

Thr Ser Leu Pro Phe Gln Asn Ile His Pro Ile Thr Ile Gly Lys Cys
305 310 315 320

Pro Lys Tyr Val Lys Ser Thr Lys Leu Arg Leu Ala Thr Gly Leu Arg
325 330 335

Asn Ile Pro Ser Ile Gln Ser Arg Gly Leu Phe Gly Ala Ile Ala Gly
340 345 350

Phe Ile Glu Gly Gly Trp Thr Gly Met Val Asp Gly Trp Tyr Gly Tyr
355 360 365

His His Gln Asn Glu Gln Gly Ser Gly Tyr Ala Ala Asp Leu Lys Ser
370 375 380

Thr Gln Asn Ala Ile Asp Glu Ile Thr Asn Lys Val Asn Ser Val Ile
385 390 395 400

Glu Lys Met Asn Thr Gln Phe Thr Ala Val Gly Lys Glu Phe Asn His
405 410 415

Leu Glu Lys Arg Ile Glu Asn Leu Asn Lys Lys Val Asp Asp Gly Phe
420 425 430

Leu Asp Ile Trp Thr Tyr Asn Ala Glu Leu Leu Val Leu Leu Glu Asn
435 440 445

Glu Arg Thr Leu Asp Tyr His Asp Ser Asn Val Lys Asn Leu Tyr Glu
450 455 460

Lys Val Arg Ser Gln Leu Lys Asn Asn Ala Lys Glu Ile Gly Asn Gly
465 470 475 480

Cys Phe Glu Phe Tyr His Lys Cys Asp Asn Thr Cys Met Glu Ser Val
485 490 495

Lys Asn Gly Thr Tyr Asp Tyr Pro Lys Tyr Ser Glu Glu Ala Lys Leu
500 505 510

Asn Arg Glu Glu Ile Asp Gly Val Lys Leu Glu Ser Thr Arg Ile Tyr
515 520 525

Gln Ile Leu Ala Ile Tyr Ser Thr Val Ala Ser Ser Leu Val Leu Val
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 29
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

Asn Pro Glu Cys Glu Ser Leu Ser Thr Ala Ser Ser Trp Ser Tyr Ile

-continued

```
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ile Ala Asp Gln Gln Thr Ile
        195                 200                 205

Tyr Gln Asn Ser Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510
```

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 30
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Thr Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Thr Ile
        195                 200                 205

Tyr Gln Asn Ser Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn

```
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 31
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80
```

-continued

```
Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Thr Ile
        195                 200                 205

Tyr Gln Asn Ser Asp Thr His Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
```

-continued

```
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 32
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Glu
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Thr Ile
        195                 200                 205

Tyr Gln Asn Ser Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285
```

Val His Asp Cys Asn Thr Thr Cys Gln Thr Pro Lys Gly Ala Ile Asn
290 295 300

Thr Ser Leu Pro Phe Gln Asn Ile His Pro Ile Thr Ile Gly Lys Cys
305 310 315 320

Pro Lys Tyr Val Lys Ser Thr Lys Leu Arg Leu Ala Thr Gly Leu Arg
325 330 335

Asn Ile Pro Ser Ile Gln Ser Arg Gly Leu Phe Gly Ala Ile Ala Gly
340 345 350

Phe Ile Glu Gly Gly Trp Thr Gly Met Val Asp Gly Trp Tyr Gly Tyr
355 360 365

His His Gln Asn Glu Gln Gly Ser Gly Tyr Ala Ala Asp Leu Lys Ser
370 375 380

Thr Gln Asn Ala Ile Asp Glu Ile Thr Asn Lys Val Asn Ser Val Ile
385 390 395 400

Glu Lys Met Asn Thr Gln Phe Thr Ala Val Gly Lys Glu Phe Asn His
405 410 415

Leu Glu Lys Arg Ile Glu Asn Leu Asn Lys Lys Val Asp Asp Gly Phe
420 425 430

Leu Asp Ile Trp Thr Tyr Asn Ala Glu Leu Leu Val Leu Leu Glu Asn
435 440 445

Glu Arg Thr Leu Asp Tyr His Asp Ser Asn Val Lys Asn Leu Tyr Glu
450 455 460

Lys Val Arg Ser Gln Leu Lys Asn Asn Ala Lys Glu Ile Gly Asn Gly
465 470 475 480

Cys Phe Glu Phe Tyr His Lys Cys Asp Asn Thr Cys Met Glu Ser Val
485 490 495

Lys Asn Gly Thr Tyr Asp Tyr Pro Lys Tyr Ser Glu Glu Ala Lys Leu
500 505 510

Asn Arg Glu Glu Ile Asp Gly Val Lys Leu Glu Ser Thr Arg Ile Tyr
515 520 525

Gln Ile Leu Ala Ile Tyr Ser Thr Val Ala Ser Ser Leu Val Leu Val
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 33
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

-continued

```
Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Glu Glu Val Leu Val
            180                 185                 190

Leu Trp Gly Ile His His Pro Ser Thr Ser Ala Asp Gln Gln Thr Ile
        195                 200                 205

Tyr Gln Asn Ser Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495
```

Lys Asn Gly Thr Tyr Asp Tyr Pro Lys Tyr Ser Glu Glu Ala Lys Leu
500 505 510

Asn Arg Glu Glu Ile Asp Gly Val Lys Leu Glu Ser Thr Arg Ile Tyr
515 520 525

Gln Ile Leu Ala Ile Tyr Ser Thr Val Ala Ser Ser Leu Val Leu Val
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 34
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

Asn Pro Glu Cys Glu Ser Leu Ser Thr Ala Ser Ser Trp Ser Tyr Ile
85 90 95

Val Glu Thr Pro Ser Ser Asp Asn Gly Thr Cys Tyr Pro Gly Asp Phe
100 105 110

Ile Asp Tyr Glu Glu Leu Arg Glu Gln Leu Ser Ser Val Ser Ser Phe
115 120 125

Glu Arg Phe Glu Ile Phe Pro Lys Thr Ser Ser Trp Pro Asn His Asp
130 135 140

Ser Asn Lys Gly Val Thr Ala Ala Cys Pro His Ala Gly Ala Lys Ser
145 150 155 160

Phe Tyr Lys Asn Leu Ile Trp Phe Val Gln Lys Gly Asn Ser Tyr Pro
165 170 175

Lys Leu Ser Lys Ser Tyr Ile Asn Asp Lys Gly Lys Glu Val Leu Val
180 185 190

Leu Trp Gly Ile His His Pro Ser Thr Ser Ala Asp Gln Gln Thr Ile
195 200 205

Tyr Gln Asn Ser Asp Thr Tyr Val Phe Val Gly Ser Ser Arg Tyr Ser
210 215 220

Lys Lys Phe Lys Pro Glu Ile Ala Ile Arg Pro Lys Val Arg Asp Gln
225 230 235 240

Glu Gly Arg Met Asn Tyr Tyr Trp Thr Leu Val Glu Pro Gly Asp Lys
245 250 255

Ile Thr Phe Glu Ala Thr Gly Asn Leu Val Val Pro Arg Tyr Ala Phe
260 265 270

Ala Met Glu Arg Asn Ala Gly Ser Gly Ile Ile Ile Ser Asp Thr Pro
275 280 285

```
Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 35
<211> LENGTH: 47
<212> TYPE: PRT
<213> ORGANISM: Influenza A virus

<400> SEQUENCE: 35

Asn His Asp Ser Asn Lys Gly Val Thr Ala Ala Cys Pro His Ala Gly
1               5                   10                  15

Ala Lys Ser Phe Tyr Lys Asn Leu Ile Trp Leu Val Lys Lys Gly Asn
            20                  25                  30

Ser Tyr Pro Lys Leu Ser Lys Ser Tyr Ile Asn Asp Lys Gly Lys
        35                  40                  45


<210> SEQ ID NO 36
<211> LENGTH: 46
<212> TYPE: PRT
<213> ORGANISM: Influenza A virus

<400> SEQUENCE: 36
```

```
Gln His Thr Thr Thr Gly Gly Ser Gln Ala Cys Ala Val Ser Gly Asn
1               5                   10                  15

Pro Ser Phe Phe Arg Asn His Val Trp Leu Thr Lys Lys Gly Asn Ser
            20                  25                  30

Tyr Pro Lys Leu Lys Gly Ser Tyr Asn Asn Thr Ser Gly Glu
        35                  40                  45
```

```
<210> SEQ ID NO 37
<211> LENGTH: 47
<212> TYPE: PRT
<213> ORGANISM: Influenza A virus

<400> SEQUENCE: 37

Thr Gly Ala Thr Gln Asn Gly Thr Ser Ser Ala Cys Ile Arg Arg Ser
1               5                   10                  15

Lys Asn Ser Phe Phe Ser Arg Leu Asn Trp Leu Thr His Leu Asn Phe
            20                  25                  30

Lys Tyr Pro Ala Leu Asn Val Thr Met Pro Asn Asn Glu Gln Phe
        35                  40                  45
```

```
<210> SEQ ID NO 38
<211> LENGTH: 48
<212> TYPE: PRT
<213> ORGANISM: Influenza A virus

<400> SEQUENCE: 38

Ser Thr Val Lys Gln Asn Gly Lys Ser Gly Ala Cys Lys Arg Ala Asn
1               5                   10                  15

Val Asn Asp Phe Phe Asn Arg Leu Asn Trp Leu Thr Lys Ser Asp Gly
            20                  25                  30

Asn Ala Tyr Pro Leu Gln Asn Leu Thr Lys Ile Asn Asn Gly Asp Tyr
        35                  40                  45
```

```
<210> SEQ ID NO 39
<211> LENGTH: 47
<212> TYPE: PRT
<213> ORGANISM: Influenza A virus

<400> SEQUENCE: 39

Asn His Asp Ala Ser Ser Gly Val Ser Ser Ala Cys Pro Tyr Asn Gly
1               5                   10                  15

Arg Ser Ser Phe Phe Arg Asn Val Val Trp Leu Ile Lys Lys Asn Asn
            20                  25                  30

Ala Tyr Pro Thr Ile Lys Arg Thr Tyr Asn Asn Thr Asn Val Glu
        35                  40                  45
```

```
<210> SEQ ID NO 40
<211> LENGTH: 48
<212> TYPE: PRT
<213> ORGANISM: Influenza A virus

<400> SEQUENCE: 40

Gly Val Asp Thr Ser Ser Gly Val Thr Gln Ala Cys Pro Tyr Asn Ser
1               5                   10                  15

Gly Ser Ser Phe Tyr Arg Asn Leu Leu Trp Ile Ile Ser Thr Lys Ser
            20                  25                  30

Ala Ala Tyr Pro Val Ile Lys Gly Thr Tyr Lys Asn Thr Gly Asn Gln
        35                  40                  45
```

<210> SEQ ID NO 41
<211> LENGTH: 49
<212> TYPE: PRT
<213> ORGANISM: Influenza A virus

<400> SEQUENCE: 41

```
Ser Gly Ile Arg Thr Asn Gly Ala Thr Ser Ala Cys Arg Arg Ser Gly
1               5                   10                  15

Ser Ser Phe Tyr Arg Ala Glu His Lys Trp Leu Leu Ser Asn Ser Asp
            20                  25                  30

Asn Ala Ala Phe Pro Gln Met Thr Lys Ser Tyr Arg Asn Pro Arg Asn
        35                  40                  45

Lys
```

<210> SEQ ID NO 42
<211> LENGTH: 47
<212> TYPE: PRT
<213> ORGANISM: Influenza A virus

<400> SEQUENCE: 42

```
Val Ile Ser Ser Gly Thr Ser Lys Ala Cys Asn Ala Ser Thr Gly Gly
1               5                   10                  15

Gln Ser Phe Tyr Arg Ser Ile Asn Trp Leu Thr Lys Lys Lys Pro Asp
            20                  25                  30

Thr Tyr Asp Phe Asn Asn His Asp Ser Asn Lys Gly Val Thr Ala
        35                  40                  45
```

<210> SEQ ID NO 43
<211> LENGTH: 42
<212> TYPE: PRT
<213> ORGANISM: Influenza A virus

<400> SEQUENCE: 43

```
Val Thr Ile Tyr Ser Gly Thr Ser Lys Ala Cys Ser Asp Ser Phe Tyr
1               5                   10                  15

Arg Ser His Arg Trp Leu Thr Gln Lys Asn Asn Ala Tyr Pro Ile Gln
            20                  25                  30

Asp Ala Gln Tyr Thr Asn Asn Gln Glu Lys
        35                  40
```

<210> SEQ ID NO 44
<211> LENGTH: 49
<212> TYPE: PRT
<213> ORGANISM: Influenza A virus

<400> SEQUENCE: 44

```
Ser Ser Ile Asn Ser Ala Gly Thr Thr Lys Ala Cys Met Arg Asn Gly
1               5                   10                  15

Gly Asn Ser Phe Tyr Ala Arg Leu Glu Trp Leu Val Ser Lys Ser Lys
            20                  25                  30

Gly Gln Asn Phe Pro Gln Thr Thr Asn Thr Tyr Arg Asn Thr Asp Ser
        35                  40                  45

Ala
```

<210> SEQ ID NO 45
<211> LENGTH: 47
<212> TYPE: PRT
<213> ORGANISM: Influenza A virus

<400> SEQUENCE: 45

-continued

```
Ala Val Asn Ser Gly Ala Gly Val Thr Ala Ala Cys Lys Phe Gly Ser
1               5                   10                  15

Ser Asn Ser Phe Phe Arg Asn His Val Trp Leu Ile His Gln Ser Gly
            20                  25                  30

Thr Tyr Pro Val Ile Arg Arg Thr Phe Asn Asn Thr Lys Gly Arg
        35                  40                  45


<210> SEQ ID NO 46
<211> LENGTH: 46
<212> TYPE: PRT
<213> ORGANISM: Influenza A virus

<400> SEQUENCE: 46

Val Ile Tyr Thr Gly Thr Ser Lys Ala Cys Asn Asn Thr Ser Asn Lys
1               5                   10                  15

Gly Ser Phe Tyr Arg Ser His Arg Trp Leu Thr Leu Lys Ser Gly Gln
            20                  25                  30

Phe Pro Val Gln Thr Asp Glu Tyr Lys Asn Thr Arg Asp Ser
        35                  40                  45


<210> SEQ ID NO 47
<211> LENGTH: 45
<212> TYPE: PRT
<213> ORGANISM: Influenza A virus

<400> SEQUENCE: 47

Glu Val Asn Asp Gly Val Ser Ser Ala Cys Lys Asp Lys Gly Ala Ser
1               5                   10                  15

Ser Phe Tyr Arg Asn Leu Val Trp Phe Val Lys Arg Gly Asn Thr Tyr
            20                  25                  30

Pro Val Ile Arg Val Gly Tyr Asn Asn Thr Thr Gly Arg
        35                  40                  45


<210> SEQ ID NO 48
<211> LENGTH: 48
<212> TYPE: PRT
<213> ORGANISM: Influenza A virus

<400> SEQUENCE: 48

Asn Gly Val Lys Val Asp Gly Ser Ser Ser Ala Cys Leu Arg Gly Gly
1               5                   10                  15

Arg Asn Ser Phe Phe Thr Arg Leu Asn Trp Leu Thr Lys Ala Thr Asn
            20                  25                  30

Gly Asn Tyr Gly Pro Ile Asn Val Thr Lys Glu Asn Thr Gly Ser Tyr
        35                  40                  45


<210> SEQ ID NO 49
<211> LENGTH: 49
<212> TYPE: PRT
<213> ORGANISM: Influenza A virus

<400> SEQUENCE: 49

Ser Gly Ile Arg Thr Asp Gly Ala Thr Ser Ala Cys Lys Arg Thr Ala
1               5                   10                  15

Ser Ser Phe Tyr Arg Ser Glu His Lys Trp Leu Ser Ser Ser Met Asn
            20                  25                  30

Asn Gln Val Phe Pro Gln Leu Asn Gln Thr Tyr Arg Asn Thr Arg Lys
        35                  40                  45

Glu
```

-continued

```
<210> SEQ ID NO 50
<211> LENGTH: 45
<212> TYPE: PRT
<213> ORGANISM: Influenza A virus

<400> SEQUENCE: 50

Asn Val Leu Asp Gly Val Thr Ala Ser Cys Leu Asp Arg Gly Ala Ser
1               5                   10                  15

Ser Phe Tyr Arg Asn Leu Val Trp Leu Val Lys Gln Asn Gly Lys Tyr
            20                  25                  30

Pro Ile Ile Lys Gly Asp Tyr Asn Asn Thr Thr Gly Arg
        35                  40                  45


<210> SEQ ID NO 51
<211> LENGTH: 44
<212> TYPE: PRT
<213> ORGANISM: Influenza A virus

<400> SEQUENCE: 51

Gly Val Thr Thr Asn Asn Val Asp Gln Thr Cys Pro Phe Glu Gly Lys
1               5                   10                  15

Pro Ser Phe Arg Tyr Asn Leu Asn Trp Ile Gln Gly Asn Ser Gly Leu
            20                  25                  30

Pro Phe Asn Ile Glu Ile Lys Asn Pro Thr Ser Asn
        35                  40


<210> SEQ ID NO 52
<211> LENGTH: 45
<212> TYPE: PRT
<213> ORGANISM: Influenza A virus

<400> SEQUENCE: 52

Asp Val Ile Thr Asn Asn Val Asp Ser Ala Cys Pro Tyr Asp Ile Asn
1               5                   10                  15

Gly Ala Ser Phe Tyr Arg Asn Leu Asn Trp Val Gln Gln Asn Lys Gly
            20                  25                  30

Lys Gln Leu Ile Phe His Tyr Gln Asn Ser Glu Asn Asn
        35                  40                  45
```